(12) United States Patent
Bornscheuer et al.

(10) Patent No.: US 8,304,223 B2
(45) Date of Patent: Nov. 6, 2012

(54) ISOFORMS OF PIG LIVER ESTERASE

(75) Inventors: Uwe Bornscheuer, Greifswald (DE); Anke Hummel, Titz (DE); Dominique Böttcher, Sponholz (DE); Elke Brüsehaber, Greifswald (DE); Kai Doderer, Rodgau (DE); Harald Trauthwein, Bürstadt (DE)

(73) Assignee: Enzymicals AG, Greifswald (DE)

( * ) Notice: Subject to any disclaimer, the term of this patent is extended or adjusted under 35 U.S.C. 154(b) by 263 days.

(21) Appl. No.: 12/532,347

(22) PCT Filed: Mar. 11, 2008

(86) PCT No.: PCT/EP2008/052880
§ 371 (c)(1),
(2), (4) Date: Sep. 21, 2009

(87) PCT Pub. No.: WO2008/116745
PCT Pub. Date: Oct. 2, 2008

(65) Prior Publication Data
US 2011/0207186 A1  Aug. 25, 2011

(30) Foreign Application Priority Data
Mar. 23, 2007  (DE) .......................... 10 2007 014 742

(51) Int. Cl.
*C12N 9/18* (2006.01)
(52) U.S. Cl. .... 435/197; 435/19; 435/252.3; 435/320.1; 536/23.2
(58) Field of Classification Search ................ 435/197, 435/19, 252.3, 320.2; 536/23.2
See application file for complete search history.

(56) References Cited

U.S. PATENT DOCUMENTS
7,229,817 B2  6/2007  Bornscheuer et al.

FOREIGN PATENT DOCUMENTS
DE  100 61 864 A1  7/2002
DE  102 58 327 A1  6/2004
WO  WO 2004/055177 A2  7/2004

OTHER PUBLICATIONS

International Search Report for PCT/EP2008/052880 filed Mar. 11, 2008.
Written Opinion of the International Searching Authority for PCT/EP2008/052880 filed Mar. 11, 2008.
International Preliminary Report on Patentability for PCT/EP2008/052880 filed Mar. 11, 2008.
English language translation of the International Preliminary Report on Patentability for PCT/EP2008/052880 filed Mar. 11, 2008.
Böttcher, et al., "Functional expression of the γ-isoenzyme of pig liver carboxyl esterase in *Escherichia coli*," *Appl. Microbiol. Biotechnol.* 73(6):1282-1289 (2007).
Brüsehaber, et al., "Identification of pig liver esterase variants by tandem mass spectroscopy analysis and their characterization," *Appl. Microbiol. Biotechnol.* 76:853-859 (2007).
David, et al., "Purification and molecular cloning of porcine intestinal glycerol-ester hydrolase," *Eur. J. Biochem.* 257:142-148 (1998).
Farb, et al., "Different Forms of Pig Liver Esterase," *Arch. Biochem. Biophys.* 203(1):214-226 (Aug. 1980).
Heymann, et al., "Characterization of the Isoenzymes of Pig-Liver Esterase," *Eur. J. Biochem.* 95:509-518 (1979).
Jones, et al., Esterases in organic synthesis: present and future, *Pure & Appl. Chem.* 62(7):1445-1448 (1990).
Jones, et al., "Enzymes in organic synthesis. 33. Stereoselective pig liver esterase-catalyzed hydrolyses of *meso* cyclopentyl-, tetrahydrofuranyl-, and tetrahydrothiophenyl-1,3-diesters," *Can. J. Chem.* 63:452-456 (1985).
Junge, et al., "Characterization of the Isoenzymes of Pig-Liver Esterase," *Eur. J. Biochem.* 95:519-525 (1979).
Lam, et al., "Enzymes in Organic Synthesis. 42. Investigation of the Effects of the Isozymal Composition of Pig Liver Esterase on Its Stereoselectivity in preparative-Scale Ester Hydrolyses of Asymmetric Synthetic Value," *J. Am. Chem. Soc.* 110:4409-4411 (1988).
Lam, et al., Enzymes in Organic Synthesis. 35 Stereoselective Pig Liver Esterase Catalyzed Hydrolyses of 3-Substituted Glutarate Diesters. Optimization of Enantiomeric Excess via Reaction Conditions Control, *J. Org. Chem.* 51:2047-2050 (1986).
Lange, et al., "Cloning, Functional Expression, and Characterization of Recombinant Pig Liver Esterase," *ChemBioChem* 2:576-582 (2001).
Matsushima, et al., "The nucleotide and deduced amino acid sequences of porcine liver proline-β-naphthylamidase," *FEBS* 293:37-41 (Nov. 1991).
Musidlowska-Persson, et al., "Site directed mutagenesis of recombinant pig liver esterase yields mutants with altered enantioselectivity," *Tetrahedron: Asymmetry* 14:1341-1344 (2003).
Musidlowska-Persson, et al., "Substrate specificity of the γ-isoenzyme of recombinant pig liver esterase towards acetates of secondary alcohols," *J. Mo. Catal. B. Enzym.* 19-20:129-133 (2002).
Seebach, et al., :Enantioselective Cleavage of *meso*-Nitrodiol Diacetates by an Esterase Concentrate from Fresh Pig Liver: Preparation of Useful Nitroaliphatic Building Blocks for EPC Syntheses, *25 Chimia* 40(9):315-318 (Sep. 1986).
Takahashi, et al., "Purification and Characterization of Proline-β-naphthylamidase, a Novel Enzyme from Pig Intestinal Mucosa," *J. Biol. Chem.* 264(20):11565-11571 (Jul. 1989).
Takahashi, et al., "Electron microscopic and biochemical evidence that proline-β-naphthylamidase is composed of three identical subunits," *FEBS* 280(2):297-300 (Mar. 1991).
Thomas, et al., "Divergent Effects of Chaperone Overexpression and Ethanol Supplementation on Inclusion Body Formation in Recombinant *Escherichia coli*," *Protein Expression and Purification* 11:289-296 (1997).

*Primary Examiner* — Tekchand Saidha
(74) *Attorney, Agent, or Firm* — Law Office of: Michael A. Sanzo, LLC

(57) ABSTRACT

The invention relates to novel mutants of γPLE, to vehicles containing the same and to their use in the production of enantiomer-enriched alcohols, carboxylic acids and esters.

19 Claims, 4 Drawing Sheets 1　2　3　4

— 1.5 kbp 1 2 3

Figure 3:

ISOFORMS OF PIG LIVER ESTERASE

CROSS REFERENCE TO RELATED APPLICATIONS

The present application is US national stage of international application PCT/EP2008/052880, which had an international filing date of Mar. 11, 2008, and which claimed priority to German application 102007014742.4, filed on Mar. 23, 2007. The international application was published in German under PCT Article 21(2) on Oct. 2, 2008. All prior applications are hereby incorporated by reference in their entirety.

The present invention relates to isoforms of pig liver esterase (γPLE), to vehicles containing the same and to their use in the production of enantiomerically enriched alcohols and esters.

Lipases and esterases can be used as efficient biocatalysts for preparing a multiplicity of optically active compounds. However, while a substantial number of lipases—in particular those of microbial origin—are commercially available, only very few esterases are available in industrial-scale quantities for the use in the resolution of racemates [Bornscheuer, U. T. and Kazlauskas R. J., Hydrolases in Organic Synthesis (2005), 2nd ed, Wiley-VCH, Weinheim].

Of particular interest here is pig liver esterase owing to its interesting catalytic properties in organic synthesis [Faber, K., Biotransformations in Organic Chemistry (2004), 5th ed. Springer, Berlin; Jones, J. B. Pure Appl. Chem, (1990), 62, 1445-1448, Jones et. al. Can. J. Chem. (1985), 63, 452-456; Lam, L. K. P. et. al., J. Org. Chem. (1986), 51, 2047-2050).

Although it has been demonstrated that esterase extracts from pig liver tissue can partly convert substrates with good stereoselectivity, the use of such extracts has a number of disadvantages, however. A particular problem with respect to stereoselectivities can be considered that of the presence of further hydrolases, in addition to fluctuations of the proportion of esterase between various batches (Seebach, D. et. al, 25 Chimia (1986), 40, 315-318). There is the additional problem that the conventional extracts consist of a plurality of isoenzymes (Farb, D., et. al, Arch. Biochem. Biophys. (1980) 203, 214-226), whose substrate specificities differ considerably in some cases. Heymann, E. and Junge, W. (Eur. J. Biochem. (1979), 95, 509-518; Eur. J. Biochem. (1979), 95, 519-525) performed a complicated electrophoretic separation, thereby isolating fractions which preferably cleave butyrylcholine, proline-β-naphthylamide and methyl butyrate. In contrast, other studies (for example Lam, L. K. P., et. al, J. Am. Chem. Soc. (1988) 110, 4409-4411) merely show individual fractions having different activities but not different specificities.

Although the cloning of putative pig liver esterase genes has been known for some time (Takahashi, T, et. al., J. Biol. Chem. (1989), 264, 11565-11571; FEBS Lett. (1991), 280, 297-300; FEBS Lett. (1991), 293, 37-41; David, L. et. al, Eur. J. Biochem. (1998) 257, 142-148), functional, recombinant expression of an active pig liver esterase has been described previously only in *Pichia pastoris* (Lange, S. et al., ChemBioChem (2001), 2, 576-582) and *E. coli* (DE 10061864).

The literature likewise describes additions to the medium during expression in *E. coli*. Addition of ethanol up to 3% (v/v) to the medium induces the formation of endogenous *E. coli* chaperones, enzymes which assist the folding process and normally support correct folding (Thomas, J G, Protein Expression and Purif (1997), 11, 289-296). However, expression of pig liver esterase in *E. coli* Origami, with the addition of 3% (v/v) ethanol to the medium, produced no detectable active esterase expression in *E. coli* but only inclusion bodies.

DE10061864 proposes coexpression of particular chaperones and γPLE. In this way it was possible to generate for the first time active γPLE from *E. coli*.

In summary it may be said that, although expression of native pig liver esterase from *E. coli* is possible, it has not yet been established on an industrial scale. It is furthermore useful and necessary to improve the (substrate) activities of pig liver esterases, in order to additionally obtain improved systems which can be employed preferably on industrial scale within the framework of biosynthetic preparation of chemical intermediates.

It was therefore an object of the present invention to specify novel esterases which are improved over the prior art. It was intended to provide novel esterases having improved activity and/or selectivity and/or stability. These esterases should be superior to those of the prior art in particular with regard to space/time yield and enantioselectivity during conversion and altered or extended substrate specificity.

This object is achieved according to the claims.

Providing esterases according to Seq. ID No. 2, having at least one mutation, selected from the group consisting of:

| Position | Amino acid |
| --- | --- |
| 94 | E |
| 96 | I |
| 97 | A, G |
| 98 | G |
| 101 | L |
| 108 | R |
| 113 | I |
| 114 | P |
| 150 | V |
| 154 | S |
| 155 | T |
| 159 | L |
| 160 | A |
| 255 | F |
| 257 | A |
| 258 | G |
| 306 | P |
| 307 | F |
| 308 | A |
| 311 | L |
| 315 | P |
| 323 | T |
| 480 | A |
| 482 | F |
| 484 | R, | surprisingly results in species which fulfill the objects mentioned. More specifically, mutations at these sites can modify and improve substrate specificity, enantioselectivity and/or activity of the native γPLE. The position here naturally refers to the first amino acid of Seq. ID No. 2.

Preference is given to esterases according to Seq. ID Nos. 4, 6, 8 and 10. These have superior activity and/or selectivity and/or stability over native γPLE. The esterases of the invention are distinguished in particular with regard to activities, enantioselectivities and other substrate specificities.

In another embodiment, the present invention relates to isolated nucleic acid coding for an esterase of the invention. Preferred nucleic acid sequences are those of Seq. ID Nos. 3, 5, 7 and 9 or their complementary form.

In a further development, the present invention relates to genes, recombinant expression systems (for example microorganisms) or recombinant plasmids/vectors having one or more of the nucleic acids of the invention.

An expression system means a system for recombinant expression of the nucleic acids of the invention and thereby for recombinant production of the polypeptides of the invention. Said production may preferably take place in microorganisms or other hosts transformed or transfected (the terms "transformation" and "transfection" are used synonymously according to the present invention) with corresponding nucleic acid sequences or vectors (see hereinbelow). Transformation and transfection may be carried out according to known methods, for example by calcium phosphate coprecipitation, lipofection, electroporation, PEG/DMSO method, particle bombardment or viral/bacteriophage infection. The cell of the invention may contain the recombinant nucleic acid in extrachromosomal or chromosomally integrated form. In other words: transfection/transformation may be stable or transient. Transfection and transformation protocols are known to the skilled worker (Chan and Cohen. 1979. High Frequency Transformation of *Bacillus subtilis* Protoplasts by Plasmid DNA. Mol Gen Genet. 168(1):111-5; Kieser et al. 2000. Practical *Streptomyces* Genetics. The John Innes Foundation Norwich; Sambrook et al. 1989. Molecular Cloning. A Laboratory Manual. In: second ed. Cold Spring Harbor Laboratory Press. Cold Spring Harbor. N.Y.; Irani and Rowe. 1997. Enhancement of transformation in *Pseudomonas aeruginosa* PAO1 by $Mg^{2+}$ and heat. Biotechniques 22: 54-56; Balbas, P. and Bolivar, F. (1990), Design and construction of expression plasmid vectors in *E. coli*, Methods Enzymol. 185, 14-37; Rodriguez, R. L. and Denhardt, D. T (eds) (1988), Vectors: a survey of molecular cloning vectors and their uses, 205-225, Butterworth, Stoneham). For the general procedures (PCR, cloning, expression etc.), reference is also made to the following literature and the citations therein: Universal GenomeWalker™ Kit User Manual, Clontech, March 2000; Triglia T.; Peterson, M. G. and Kemp, D. J. (1988), A procedure for in vitro amplification of DNA segments that lie outside the boundaries of known sequences, Nucleic Acids Res. 16, 8186.

The host is preferably a recombinant microorganism of prokaryotic origin. Suitable host cells include cells of unicellular microorganisms such as bacterial cells. Microorganisms which may be mentioned in this regard are prokaryotes such as *E. coli, Bacillus subtilis*. Other bacteria which may be employed for expression of the nucleic acid sequences of the invention are those of the genera/species *Lactobacillus, Bacillus, Rhodococus, Campylobacter, Caulobacter, Mycobacterium, Streptomyces, Neisseria, Ralstonia, Pseudomonas*, and *Agrobacterium*. Preference is given to utilizing *E. coli* strains for this purpose. Very particular preference is given to: *E. coli* XL1 Blue, NM 522, JM101, JM109, JM105, RR1, DH5α, TOP 10-, HB101, BL21 codon plus, BL21 (DE3) codon plus, BL21, Rosetta, Rosetta-gami, MM294, W3110, DSM14459 (EP1444367), Origami. Corresponding strains are available in the prior art and may, at least partly, be obtained via the international depositary institutions such as ATCC or DMSZ.

It is likewise possible to employ eukaryotes such as mammalian cells, insect cells or plant cells, or organisms such as, for example, yeasts such as Hansenula polymorpha, *Pichia* sp., *Saccharomyces cerevisiae*, or fungi such as, for example, *Aspergillus* sp., for recombinant production of the polypeptides. Suitable eukaryotic cells include CHO cells, HeLa cells and others. Many of these cells can be obtained via depositary institutions such as ATCC or DMSZ.

The polypeptides of the invention may also be recombinantly prepared in a non-human host. The non-human host may be a cell or a multi- to polycellular organism. Suitable polycellular organisms include model systems familiar in molecular biology, such as *Drosophila melanogaster*, Zebrafisch or *C. elegans*. Transgenic non-human animals may be produced by methods known in the prior art. The transgenic non-human animal of the invention may preferably have different genetic constitutions. It may (i) overexpress the gene of a nucleic acid sequence of the invention constitutively or inducibly, (ii) contain an inactivated form of the endogenous gene of a nucleic acid sequence of the invention, (iii) contain a mutated gene of a nucleic acid sequence of the invention, which gene replaces completely or partly the endogenous gene of a nucleic acid sequence of the invention, (iv) have conditional and tissue-specific overexpression or underexpression of the gene of a nucleic acid sequence of the invention, or (v) have a conditional and tissue-specific knockout of the gene of a nucleic acid sequence of the invention.

The transgenic animal preferably contains in addition an exogenous gene of a nucleic acid sequence of the invention under control of a promoter allowing overexpression. Alternatively, the endogenous gene of a nucleic acid sequence of the invention may be overexpressed by activating or/and replacing the endogenous promoter. Preferably, the endogenous promoter of the gene of a nucleic acid sequence of the invention has a genetic modification which results in increased expression of said gene. Genetic modification of the endogenous promoter comprises both a mutation of individual bases and deletion and insertion mutations. In a particularly preferred embodiment of the host of the invention, said host is a transgenic rodent, preferably a transgenic mouse, a transgenic rabbit, a transgenic rat, or a transgenic sheep, a transgenic cow, a transgenic goat or a transgenic pig. Mice have numerous advantages over other animals. They are easy to keep and their physiology is regarded as a model system for that of humans. The production of such genetically manipulated animals is sufficiently known to the skilled worker and is performed by conventional methods (see, for example, Hogan, B., Beddington, R., Costantini, F. and Lacy, E. (1994), Manipulating the Mouse-Embryo; A Laboratory Manual, 2nd edition., Cold Spring Harbor Laboratory, Cold Spring Harbor, N.Y.; WO91/08216). Alternatively or additionally, it is also possible to employ cell culture systems, in particular human cell culture systems, for the applications described for the non-human transgenic animal of the invention.

Another development of the invention relates to complete genes which have the nucleic acids of the invention. Gene means according to the application a section at the molecular level, which in principle may consist of two different regions:
 a DNA section from which a single-stranded RNA copy is produced by transcription
 all additional DNA sections involved in regulating this copying process.

More detailed definitions can be found at: http://de.wikipedia.org/wiki/Gen.

The coding nucleic acid sequences may be cloned into conventional plasmids/vectors and, after transfection of microorganisms or other host cells with such vectors, be expressed in cell culture. Suitable plasmids or vectors are in principle any embodiments available to the skilled worker for this purpose. Such plasmids and vectors may be found, for example, in Studier and coworkers (Studier, W. F.; Rosenberg A. H.; Dunn J. J.; Dubendroff J. W.; Use of the T7 RNA polymerase to direct expression of cloned genes, Methods Enzymol. 1990, 185, 61-89) or the brochures of Novagen, Promega, New England Biolabs, Clontech or Gibco BRL. Other preferred plasmids and vectors may be found in: Glover, D. M. (1985), DNA cloning: a practical approach, Vol. I-III, IRL Press Ltd., Oxford; Rodriguez, R. L. and Denhardt, D. T (eds) (1988), Vectors: a survey of molecular cloning vectors and their uses, 179-204, Butterworth, Stoneham; Goeddel, D. V., Systems for heterologous gene expression, Methods Enzymol. 1990, 185, 3-7; Sambrook, J.; Fritsch, E. F. and Maniatis, T. (1989), Molecular cloning: a laboratory manual, 2nd ed., Cold Spring Harbor Laboratory Press, New York.

Plasmids which may be used for cloning the nucleic acid sequence of the invention or a gene construct containing them into the host organism in a very preferred manner are: pUC18 (Roche Biochemicals), pKK-177-3H (Roche Biochemicals), pBTac2 (Roche Biochemicals), pKK223-3 (Amersham Pharmacia Biotech), pKK-233-3 (Stratagene) or pET (Novagen). Suitable vectors are also, for example, pET-21a(+) for *E. coli*, but other expression vectors for prokaryotic unicellular organism and vectors for eukaryotes may also be used. Examples of vectors which have proved suitable for yeasts are the pREP vector and the pINT vector. Baculovirus vectors such as those in EP127839 or EP549721, for example, have been disclosed for expression in insect cells, and SV40 vectors, for example, are suitable for expression in mammalian cells and are generally available. Particular preference is given to vectors for unicellular eukaryotic organisms, in particular from the group of pET vectors, for transformation of *E. coli* cells, in particular *E. coli* Origami.

In a particularly preferred embodiment, the nucleic acid sequence of the invention, which has been introduced into the vector, is additionally fused to a histidine tag provided by said vector. Preference is given to cloning the introduced nucleic acid sequence into the preferred pET vector in such a way that transcription is under the control of the IPTG-regulatable promoter present in the vector. Alternatively, preference is also given to employing rhamnose-regulatable promoters.

Aside from the usual markers such as, for example, antibiotic resistance genes, the vectors may contain further functional nucleotide sequences for regulating, in particular repressing or inducing, the expression of the ADH gene and/or a reporter gene. Preference is given to utilizing promoters which are regulatable weak promoters such as the rha promoter or the nmtl promoter, for example, or regulatable strong promoters such as the lac, ara, lambda, pL, T7 or T3-promoter, for example. The coding DNA fragments must be transcribable from a promoter in the vectors. Other examples of established promoters are the Baculovirus polyhedrin promoter for expression in insect cells (see, for example, EP127839) and the early SV40 promoter, and LTR promoters, for example of MMTV (Mouse Mammary Tumour Virus; Lee et al. (1981) Nature, 294 (5838), 228-232).

Accordingly, the genes, vectors/plasmids of the invention may contain further functional sequence regions such as, for example, an origin of replication, operators or termination signals.

In a particularly advantageous embodiment, the present invention relates to rec microorganisms which, in addition to the nucleic acid sequence of the invention, also contain one or more cloned chaperone genes. Preferred suitable chaperones are GroEL and GroES, preferably in an *E. coli* Origami strain. Surprisingly, expression of the active enzyme was achieved in the presence of these two folding helper proteins, although other alternative chaperone systems such as, for example, the endogenous *E. coli* chaperones, induced by the addition of ethanol or other coexpressed chaperones such as DnaK, DnaJ and GrpE, were not successful (DE 10061864).

To a person skilled in the art, it comes as a surprise that equivalent coexpression of the chaperone systems Dnak, DnaJ, GrpE and GroEL, GroES, or coexpression of GroEL or GroES alone, together with pig liver esterase in *E. coli* Origami, only results in expression in the form of inclusion bodies and not in a detectable activity in *E. coli* crude cell extract. Preference is therefore in any case given to the chaperone system GroEL/GroES being the preferred induced/ expressed system, even if other chaperone systems are present in the host organism at the same time.

Functional expression of eukaryotic proteins in *E. coli* represents a formidable challenge, in particular if said proteins are posttranslationally glycosylated proteins. In the case of recombinant expression of pig liver esterase in *E. coli*, the use of the special chaperone system GroEL, GroES apparently cancels out the lack of posttranslational glycosylation. Reference is made to DE102006031600 with regard to this development and its embodiment.

In a further development, the present invention concerns the use of the (rec)polypeptides of the invention for preparing enantiomerically enriched alcohols, carboxylic acids and esters, in particular from the mesoforms of the aforementioned compounds, such as, for example, optionally substituted dicarboxylic esters such as malonic diesters.

It is possible to use the enzymes in immobilized form (Sharma B. P.; Bailey L. F. and Messing R. A. (1982), Immobilisierte Biomaterialien—Techniken und Anwendungen [Immobilized biomaterials—Techniques and applications], Angew. Chem. 94, 836-852). Immobilization is advantageously achieved by lyophilization (Paradkar, V. M.; Dordick, J. S. (1994), Aqueous-Like Activity of α-Chymotrypsin Dissolved in Nearly Anhydrous Organic Solvents, J. Am. Chem. Soc. 116, 5009-5010; Mori, T.; Okahata, Y. (1997), A variety of lipi-coated glycoside hydrolases as effective glycosyl transfer catalysts in homogeneous organic solvents, Tetrahedron Lett. 38, 1971-1974; Otamiri, M.; Adlercreutz, P.; Matthiasson, B. (1992), Complex formation between chymotrypsin and ethyl cellulose as a means to solubilize the enzyme in active form in toluene, Biocatalysis 6, 291-305). Very particular preference is given to lyophilization in the presence of surfactants such as Aerosol OT or polyvinylpyrrolidone or polyethylene glycol (PEG) or Brij 52 (diethylene glycol monocetyl ether) (Kamiya, N.; Okazaki, S.-Y.; Goto, M. (1997), Surfactant-horseradish peroxidase complex catalytically active in anhydrous benzene, Biotechnol. Tech. 11, 375-378).

Most preference is given to immobilization to Eupergit®, in particular Eupergit C® and Eupergit 250L® (Röhm) (for an overview, see: E. Katchalski-Katzir, D. M. Kraemer, J. Mol. Catal. B: Enzym. 2000, 10, 157). Preference is likewise given to immobilization to Ni-NTA in combination with the polypeptide modified by attaching a His tag (hexahistidine) (Petty, K. J. (1996), Metal-chelate affinity chromatography In: Ausubel, F. M. et al. eds. Current Protocols in Molecular Biology, Vol. 2, New York: John Wiley and Sons).

The use as CLECs is also conceivable (St. Clair, N.; Wang, Y.-F.; Margolin, A. L. (2000), Cofactor-bound cross-linked enzyme crystals (CLEC) of alcohol dehydrogenase, Angew. Chem. Int. Ed. 39, 380-383).

These measures may succeed in generating from (rec) polypeptides which are rendered unstable by organic solvents polypeptides which may work in mixtures of aqueous and organic solvents or wholly in organics.

Esters or carboxylic acids and alcohols are converted using the polypeptides of the invention preferably as follows. The polypeptides are added in the desired form (free, immobilized, in host organisms or in a randomly disrupted form) to the appropriate medium, preferably the aqueous solution. The substrate is added to this mixture, while maintaining the optimal temperature range and the optimal pH range. After the conversion has been completed, the alcohol or ester obtained may be isolated from the reaction mixture by methods known to the skilled worker (crystallization, extraction, chromatography).

Enzymatic conversion of esters or carboxylic acids and alcohols to enantiomerically enriched alcohols, carboxylic acids and esters by means of esterases is known in principle to a person skilled in the art (see references cited at the outset; diagram 2). Of particular interest in this context are the conversions of mesoforms of the aforementioned derivatives. Here the conversion of the invention is beneficial in that an enantiomerically enriched product can be obtained with a yield of 100%, while normal resolutions of the racemates can only produce a yield of up to 50% of the particular enantiomers. Thus, for example, using particular substituted malonic diesters can produce enantiomerically enriched products which are valuable intermediates in chemical synthesis. In this way it is possible to efficiently and easily produce from optionally N-protected amino malonic diesters the corresponding enantiomerically enriched asymmetric aminocarboxylic monoesters. The reaction sequence depicted in diagram 1 below is also interesting.

Diagram 1:

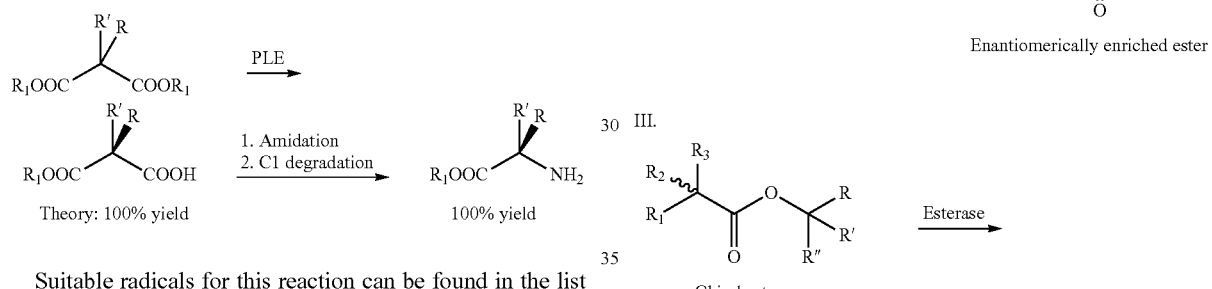

Suitable radicals for this reaction can be found in the list below.

The measures of amidation and of C1 degradation are sufficiently known to the skilled worker (Organikum, VEB Deutscher Verlag der Wissenschaften, Berlin 1986, pp. 388ff, pp. 571ff).

Diagram 2:

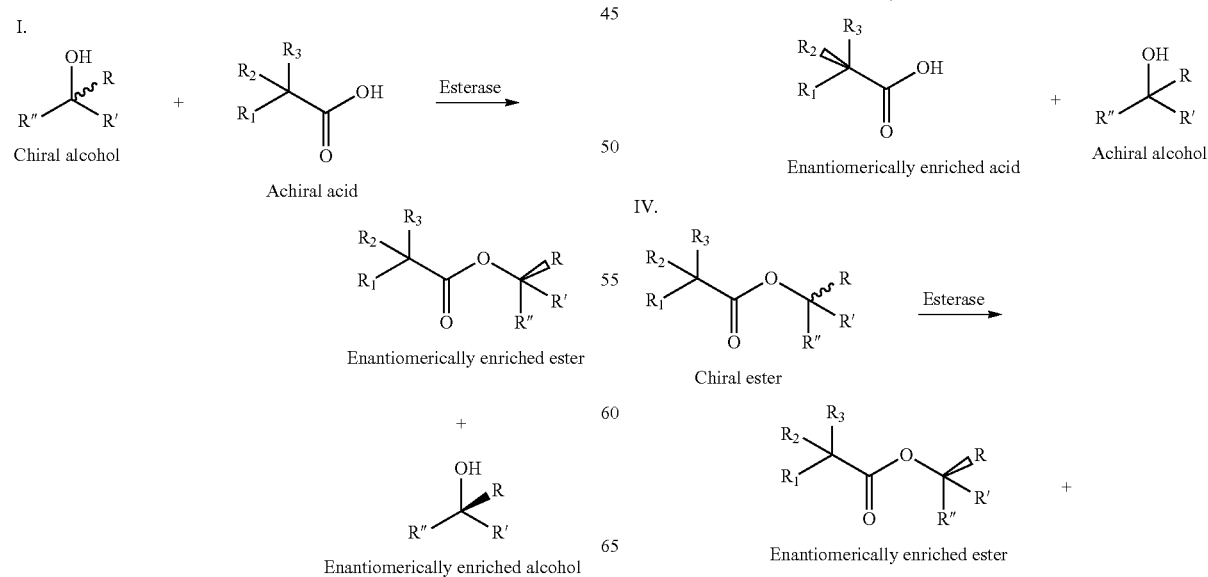

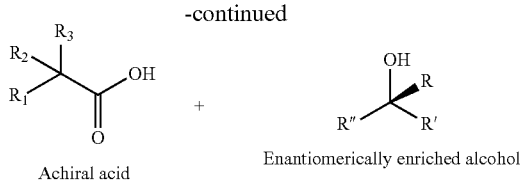

Achiral acid + Enantiomerically enriched alcohol

Examples of enantiomerically enriched alcohols which may be prepared from the corresponding chiral esters according to I, or VI, or which may be used to prepare enantiomerically enriched esters are likewise familiar to the skilled worker. They can be summarized, for example, by the following general formula,

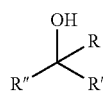

in which R, R' and R" are different from one another, in particular
H, $(C_1-C_8)$-alkyl, $(C_1-C_8)$-alkoxy, HO—$(C_1-C_8)$-alkyl, $(C_2-C_8)$-alkoxyalkyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{18})$-heteroaryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl or R and R' and/or R and R" and/or R' and R" form a $(C_3-C_5)$-alkylene bridge.

Examples of enantiomerically enriched esters or acids may be assigned to the following general formulas,

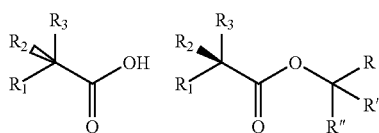

in which R, R' and R" are identical or different from one another, in particular
H, $(C_1-C_8)$-alkyl, $(C_1-C_8)$-alkoxy, HO—$(C_1-C_8)$-alkyl, $(C_2-C_8)$-alkoxyalkyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{18})$-heteroaryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl or R and R' or R and R" or R' and R" form a $(C_3-C_5)$-alkylene bridge, and $R_1$, $R_2$ and $R_3$ are different from one another, in particular
H, $(C_1-C_8)$-alkyl, $(C_1-C_8)$-alkoxy, HO—$(C_1-C_8)$-alkyl, $(C_2-C_8)$-alkoxyalkyl, cyclopentadienyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{18})$-heteroaryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl or $R_1$ and $R_2$ and/or $R_1$ and $R_3$ and/or $R_2$ and $R_3$ form a $(C_3-C_5)$-alkylene bridge.

Suitable for the use according to the invention are aqueous solvents which are suitably buffered. However, it is also possible to perform the reaction using a pH-stat instrument [company: Schott A G, Mainz, Germany, brand TitroLine alpha].

Preference is given to carrying out the conversion at a temperature of between 0° C. and 85° C., particularly preferably between 30 and 80° C., very particularly preferably at around 50° C. The skilled worker also has a free choice of pH of the reaction, and the reaction may be carried out both at a fixed pH and with the pH being varied within a pH interval. The pH is chosen in particular with regard to an optimal reaction result according to the present object. Preference is given to carrying out the reaction at a pH at from pH 5 to 9, preferably pH 6 to 8 and particularly preferably pH 6.5 to 7.5.

As already mentioned above, the polypeptide concerned may be applied in the native form by way of homogeneously purified compounds, or as a recombinantly produced enzyme. Furthermore, the (rec)polypeptide may also be employed as a component of an intact guest organism or in connection with the disrupted cell mass of the host organism, which may have any degree of purity.

If the substrate used is converted to the desired product in cell culture, for example by employing a suitable host, a suitable nutrient medium is used depending on the host organism used or the cell culture used. Suitable media for the host cells are generally known and commercially available. Moreover, the cell cultures may be supplemented with usual additives such as, for example, antibiotics, growth promoters such as, for example, sera (fetal calf serum, etc.), and similar known supplements.

Further optimal reaction conditions can be found in DE102006031600.

Another application relates to the preparation of a polypeptide having improved activity and/or selectivity and/or stability over SEQ. ID. NO: 2 polypeptide by
i) mutagenesis of the nucleic acid of the invention, preferably that of Seq. 3, 5, 7, 9,
ii) cloning of the nucleic acid sequence obtainable from i) into a suitable vector with subsequent transformation into a suitable expression system, and
iii) detection and isolation of said polypeptide having improved activity and/or selectivity and/or stability.

The procedure of improving the nucleic acid sequences of the invention or the polypeptides encoded by them by means of mutagenesis methods is well known to a skilled worker. Suitable mutagenesis methods are any methods available for this purpose to the skilled worker. These are, in particular, saturation mutagenesis, random mutagenesis, in vitro recombination methods, and site directed mutagenesis (Eigen, M. and Gardiner, W., Evolutionary molecular engineering based on RNA replication, *Pure Appl. Chem.* 1984, 56, 967-978; Chen, K. and Arnold, F., Enzyme engineering for nonaqueous solvents: random mutagenesis to enhance activity of subtilisin E in polar organic media. *Bio/Technology* 1991, 9, 1073-1077; Horwitz, M. and Loeb, L., Promoters Selected From Random DNA-Sequences, *Proc Natl Acad Sci USA* 83, 1986, 7405-7409; Dube, D. and L. Loeb, Mutants Generated By The Insertion Of Random Oligonucleotides Into The Active-Site Of The Beta-Lactamase Gene, *Biochemistry* 1989, 28, 5703-5707; Stemmer, P. C., Rapid evolution of a protein in vitro by DNA shuffling, *Nature* 1994, 370, 389-391 and Stemmer, P. C., DNA shuffling by random fragmentation and reassembly: In vitro recombination for molecular evolution. *Proc Natl Acad Sci USA* 91, 1994, 10747-10751).

The new nucleic acid sequences obtained are cloned into a host organism by the methods indicated hereinbelow (for references see below), and the polypeptides expressed in this way are detected using suitable screening methods and subsequently isolated. Suitable for detection are in principle any possible detection reactions for the molecules produced by this polypeptide. Particularly suitable for this are photometric assays for NADH produced or consumed, HPLC or GC methods for detecting the alcohols produced by this enzyme. Moreover, detection methods by means of gel electrophoresis or by means of antibodies are also suitable for detecting new polypeptides which have been modified by genetic engineering methods.

Optically enriched (enantiomerically enriched, enantiomer-enriched?) compounds mean for the purpose of the invention the presence of one optical antipode in the mixture with the other one at >50 mol %.

The term nucleic acid sequences means all kinds of single-stranded or double-stranded DNA as well as RNA or mixtures thereof. Accordingly, the nucleic acid sequence of the invention may be a DNA molecule or an RNA molecule. Preference is given to the nucleic acid molecule being a cDNA molecule or an mRNA molecule. According to the invention, the DNA molecule may also be a genomic DNA molecule. The invention furthermore comprises embodiments in which the DNA molecule is a PNA molecule or another derivative of a DNA molecule.

The term "complementary" means according to the invention that complementarity extends across the entire region of the nucleic acid molecule of the invention, without any gaps. In other words: preference is given according to the invention to 100% complementarity extending across the entire region of the sequence of the invention, i.e. from the 5' end depicted to the 3' end depicted.

Improving the activity and/or selectivity and/or stability means according to the invention that the polypeptides are more active and/or more selective and/or, under the reaction conditions used, more stabile. While activity and stability of the enzymes naturally should be as high as possible for industrial application, improvement with respect to selectivity refers to the situation in which substrate selectivity decreases but enantioselectivity of the enzymes increases. The same applies mutatis mutandis to the expression not substantially reduced, used in this context.

Of the claimed protein sequences and the nucleic acid sequences, the invention also comprises those sequences which are more than 97%, preferably more than 97.5%, 98% or 98.5%, more preferably more than 99% or 99.5%, homologous (excluding natural degeneration) to any of these sequences, as long as such a sequence retains its functionality or purpose. The expression "homology" (or identity), as used herein, may be defined by the equation $H (\%) = [1 - V/X] \times 100$, wherein H means homology, X is the total number of nucleobases/amino acids of the comparative sequence, and V is the number of different nucleobases/amino acids of the sequence to be considered, based on the comparative sequence. In any case, the term nucleic acid sequences which code for polypeptides includes any sequences that appear possible according to the degeneracy of the genetic code.

The expression "under stringent conditions" is understood herein as described in Sambrook et al. (Sambrook, J.; Fritsch, E. F. and Maniatis, T. (1989), Molecular cloning: a laboratory manual, 2nd ed., Cold Spring Harbor Laboratory Press, New York). Preferably, a hybridization is stringent according to the present invention, if, after washing with 1×SSC (150 mM sodium chloride, 15 mM sodium citrate, pH 7.0) and 0.1% SDS (sodium dodecylsulfate) at 50° C., preferably at 55° C., more preferably at 62° C. and most preferably at 68° C., for 1 hour, and more preferably with 0.2×SSC and 0.1% SDS at 50° C., more preferably at 55° C., still more preferably at 62° C. and most preferably at 68° C., for 1 hour, a positive hybridization signal is still observed.

$(C_1-C_8)$-Alkyl radicals can be considered methyl, ethyl, n-propyl, isopropyl, n-butyl, isobutyl, sec-butyl, tert-butyl, pentyl, hexyl, heptyl or octyl, and any of their binding isomers.

A $(C_1-C_{20})$-alkyl radical is, within the scope of the definition according to the invention, a corresponding radical having from 1 to up to 20 carbon atoms.

A $(C_3-C_{20})$-alkyl radical is, within the scope of the definition according to the invention, a corresponding radical having from 3 to up to 20 carbon atoms.

The radical $(C_1-C_8)$-alkoxy corresponds to the radical $(C_1-C_8)$-alkyl with the proviso that the former is bound via an oxygen atom.

$(C_2-C_8)$-Alkoxyalkyl means radicals in which the alkyl chain is interrupted by at least one oxygen function, it not being possible for two oxygen atoms to be linked to one another. The number of carbon atoms indicates the total number of carbon atoms contained in the radical.

A $(C_3-C_5)$-alkylene bridge is a carbon chain having from three to five carbon atoms, which chain is bound via two different carbon atoms to the molecule concerned.

The radicals described above may be mono- or polysubstituted with halogens and/or $(C_1-C_8)$-alkoxycarbonyl and/or N-, O-, P-, S-, Si-atom-containing radicals. The latter are in particular alkyl radicals of the above kind, whose chain has one or more of said heteroatoms or which are bound via one of these heteroatoms to the molecule.

$(C_3-C_8)$-Cycloalkyl means cyclopropyl, cyclobutyl, cyclopentyl, cyclohexyl and cycloheptyl radicals, etc. These may be substituted with one or more halogens and/or N-, O-, P-, S-, Si-atom-containing radicals, and/or may have N, O, P, S atoms in the ring, such as, for example, 1-, 2-, 3-, 4-piperidyl, 1-, 2-, 3-pyrrolidinyl, 2-, 3-tetrahydrofuryl, 2-, 3-, 4-morpholinyl.

A $(C_3-C_8)$-cycloalkyl-$(C_1-C_8)$-alkyl radical refers to a cycloalkyl radical as depicted above which is bound via an alkyl radical as indicated above to the molecule.

$(C_1-C_8)$-Alkoxycarbonyl means for the purpose of the invention an alkyl radical as defined above having up to 8 carbon atoms, which is bound via an O(C=O) function.

$(C_1-C_8)$-Acyloxy means for the purpose of the invention an alkyl radical as defined above having up to 8 carbon atoms, which is bound via a (C=O)O function.

$(C_1-C_8)$-Acyl means for the purpose of the invention an alkyl radical as defined above having up to 8 carbon atoms, which is bound via a (C=O) function.

A $(C_6-C_{18})$-aryl radical means an aromatic radical having from 6 to 18 carbon atoms. More specifically, it includes compounds such as phenyl, naphthyl, anthryl, phenanthryl, biphenyl radicals or systems of the above-described kind which are annealed to the molecule in question, such as, for example, indenyl systems, which may optionally be substituted with $(C_1-C_8)$-alkyl, $(C_1-C_8)$-alkoxy, $(C_2-C_8)$-alkoxyalkyl, $NH(C_1-C_8)$-alkyl, $N((C_1-C_8)$-alkyl$)_2$, OH, $O(C_1-C_8)$-alkyl, $NO_2$, $NH(C_1-C_8)$-acyl, $N((C_1-C_8)$-acyl$)_2$, F, Cl, $CF_3$, $(C_1-C_8)$-acyl, $(C_1-C_8)$-acyloxy, $(C_7-C_{19})$-aralkyl radical, $(C_4-C_{19})$-heteroaralkyl.

A $(C_7-C_{19})$-aralkyl radical is a $(C_6-C_8)$-aryl radical which is bound to the molecule via a $(C_1-C_8)$-alkyl radical.

A $(C_3-C_{18})$-heteroaryl radical, within the scope of the invention, refers to a five-, six- or seven-membered aromatic ring system of from 3 to 18 carbon atoms which has heteroatoms such as, for example, nitrogen, oxygen or sulfur in the ring. Such heteroaromatics are considered in particular radicals such as 1-, 2-, 3-furyl, such as 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl. The heteroaromatics may be substituted in the same way as the $(C_6-C_{18})$-aryl radicals mentioned above.

A $(C_4-C_{19})$-heteroaralkyl means a heteroaromatic system corresponding to the $(C_7-C_{19})$-aralkyl radical.

Suitable halogens (Hal) are fluorine, chlorine, bromine or iodine.

The term aqueous solvent means water or a solvent mixture which mainly consists of water and contains water-soluble organic solvents such as, for example, alcohols, in particular methanol or ethanol, or ethers, such as THF or dioxane, or other cosolvents such as DMSO.

The references cited in this document are considered to be also within the scope of the disclosure.

The protein sequences depicted in the sequence listing additionally contain a His-tag and a linker sequence on the C-terminus. The actual protein sequences which represent the active γPLEs are therefore the sequences depicted in the sequence listing, which are truncated by 21 amino acids on the C-terminus. The same applies to the nucleic acid sequences coding for said protein sequences.

BRIEF DESCRIPTION OF THE DRAWINGS

FIG. 3: Partial alignment of the amino acid sequences of the PLEs found, PLEs 2, 3, 4 and 5, with the sequence of γ-PLE (PLE 1).

Figure 1:
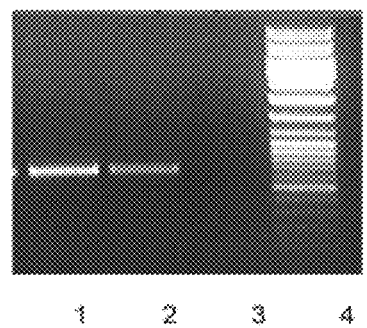
FIG. 1: cDNA quality control by amplification of the β-actin gene. Templates: lane 1: human cDNA (positive control), lane 2: cDNA from pig liver, lane 3: water (negative control).

Methods:

Isolation of mRNA and cDNA Synthesis

Fresh pig liver tissue (0.1 g) was treated with Trizol® reagent (TRIzol® Plus RNA Purification Kit, Invitrogen, Calif., USA), homogenized (10 min at RT; Ultraturrax T25, IKA-Labortechnik), and the RNA was isolated according to the manufacturer's instructions. The RNA concentration was determined spectrophotometrically. The cDNA synthesis was carried out by means of RT-PCR using oligo(dT)15 primers and MMLV reverse transcriptase with RNase H activity (Promega, Madison, Wis., USA) according to the manufacturer's protocol.

Amplification and Cloning of PLE Genes

The RT-PCR product was used for the amplification of PLE genes using two gene-specific primers based on the γPLE sequence (5'-CACCCATATGGGGCAGCCAGCCTCGC-3' (Seq. ID No. 11), with the NdeI restriction cleavage site marked in italics, and 5'-CCGCTCGAG TCACTTTATCTTGGGTGGCTTCTTTGC-3' (Seq. ID No. 12), with the XhoI restriction cleavage site marked in italics; start and stop codons are underlined). The forward primer moreover contains on its 5' end the bases CACC which make possible subsequent cloning into a TOPO vector (see below). These primers already eliminate the 18-amino-acid signal sequence attached to the N terminus of the original porcine gene, and the 4-amino-acid C terminal ER (endoplasmic reticulum) retention signal, thereby facilitating subsequent expression in E. coli (Lange, S, et. al., ChemBioChem (2001), 2, 576-582). The PCR was carried out on a thermocycler (Techne Progene, Jepson Bolton Laboratory Equipment, Watford, United Kingdom). The PCR employed Pfu Plus Polymerase (Roboklon, Berlin, Germany) according to the manufacturer's instructions and the following temperature program: after denaturation for 5 minutes at 95° C., 30 cycles of 1 min at 95° C., 1 min at 60° C., 3 min at 72° C. were carried out, with a final 7 min at 72° C. The PCR products were fractionated in an agarose gel, purified and cloned into a TOPO/pET101 according to the manufacturer's protocol (Champion™ pET Directional TOPO® Expression Kit; Invitrogen, Carlsbad, Calif., USA). E. coli TOP10 cells [F⁻ mcrA D(mrr-hsdRMSmcrBC) (F80lacZDM15) DlacX74 recA1 deoR araD139 D(ara-leu)7697 galU galK rpsL (Str$^R$) endA1 nupG] (Invitrogen) were transformed with the construct mixture and separated out on agar plates. The recombinant single clones obtained in this way were cultured separately, the plasmid DNA was isolated, identified by size determination or restriction mapping and used as template for PCR amplification of the PLE sequences. The amplified sequences were then sequenced (MWG-Biotech, Martinsried, Germany).

Construction of the Expression System

Plasmid DNA of the individual TOPO/pET101-PLE constructs were digested with NdeI and XhoI according to the manufacturer's protocol (New England Biolabs, Beverly, Mass., USA; Promega, Madison, Wis., USA), and the particular fragments of about 1694 bp in size were inserted into NdeI/XhoI-digested, agarose gel-purified pET15b vector (Novagen, Madison, Wis., USA), which adds an additional N-terminal His tag to the gene. The ligation products were used for transformation of E. coli DH5a strains (Novagen, Madison, Wis., USA) [supE44ΔlacU169 (Φ80lacZΔM15) hsdR17 recA1 endA1 gyrA96 thi-1relA1], and the plasmid was propagated by culturing the transformed strains. The plasmid was isolated from the recombinant strains and again sequenced for a check. The pET15b-PLE constructs thus obtained were used for transformation of E. coli Origami (DE 3) strains [Δ(ara-leu)7697 ΔlacX74 ΔphoA PvuII phoR araD139 ahpC galE galK rpsL F'[lac⁺ lacI$^q$ pro] (DE3) gor522::Tn10 trxB (Kan$^R$, Str$^R$, Tet$^R$)4] (Novagen, Madison, Wis., USA) which had previously been transformed with pGro7 plasmid (Chaperone Plasmid Set, TAKARA BIO Inc., Otsu, Shiga, Japan), which enables the chaperone GroEL+ GroES to be expressed.

For details of expressing pig liver esterase with coexpression of the chaperone complex GroEL/ES, see: Böttcher, D., Brüsehaber, E., Doderer. K., Bornscheuer, U. T. (2007), Functional expression of the gamma-isoenzyme of pig liver carboxyl esterase in Escherichia coli, Appl. Microbiol. Biotechnol., (2007), 73(6), 1282-1289.

Expression of Recombinant PLE Isoenzymes in E. coli Origami with Coexpression of the GroEL/ES Chaperone Complex.

The chaperones were coexpressed with the PLE isoenzymes in 150 ml of LB medium containing 20 μg mL⁻¹ chloramphenicol and 50 μg mL⁻¹ ampicillin for plasmid selection. Chaperone expression was immediately initiated by adding 1 mg mL⁻¹ L-arabinose. PLE production was induced at OD600=0.5 by adding 40 μM IPTG. The cells were removed by centrifugation after 24 h, resuspended in 10 ml of sodium phosphate buffer (50 mM, pH 7.5) and disrupted using ultrasound. Cell debris was removed by centrifugation, and the supernatant was used for further experiments (crude cell extract). Protein content and esterase activity were determined according to Bradford or using the pNPA assay.
Native Polyacrylamide Gel Electrophoresis and Activity Staining with Fast Red.

A mixture containing the crude extract of recombinantly produced PLE (5-15 µL, corresponding to 0.05-0.15 U of pNPA analysis) was mixed with buffer solution (20% (w/v) glycerol; 0.0025% (w/v) bromophenol blue in dH2O) (5-10 µL). Aliquots thereof were separated on a native polyacrylamide gel (7.5%). For activity staining, the gel was incubated in a mixture of freshly prepared α-naphthyl acetate and Fast Red. Formation of a red complex between α-naphthol generated and Fast Red indicated hydrolytic activity of the esterase. (Krebsfänger, N., et. al., (1998) Enzyme Microb. Technol, 22, 641-646). The gel was then stained with Coomassie Brilliant Blue.

Esterase Activity

Esterase activity was determined spectrophotometrically in sodium phosphate buffer (50 mM) by means of p-nitrophenyl acetate (10 mM, dissolved in dimethyl sulfoxide) as substrate. The amount of p-nitrophenol generated was determined at a wavelength of 410 nm ($\epsilon=15*10^3$ $M^{-1}$ $cm^{-1}$) at RT and pH 7.5. 1 unit (U) is defined as the amount of enzyme capable of converting 1 µM p-nitrophenol per minute under analytical conditions (Krebsfänger, N., et. al., (1998) Enzyme Microb. Technol, 22, 641-646).

Esterase substrate specificity was analyzed at constant pH. A known amount of esterase was added to an emulsion (20 mL) containing an ester substrate (5% (v/v); tributyrin, ethyl acetate, triolein or methyl butyrate) and gum arabic (2% (w/v)) at 37° C. The acid liberated was counter titrated automatically in a pH statiometer (Schott, Mainz, Germany) with 0.01 N NaOH in order to maintain a constant pH of 7.5. 1 unit (U) is defined as the amount of enzyme capable of generating 1 µM acid per minute under analytical conditions.

Stereoselectivity of Enzymatic Hydrolysis of Acetates of Secondary Alcohols
(see DE10258327A1)

Hydrolysis was carried out in 1.5 ml reaction vessels in a thermomixer (Thermomixer comfort Eppendorf, Hamburg, Germany) at 37° C. 0.5 U esterase crude extract (based on the pNPA assay) were used for 1 ml of substrate solution (10 mM in sodium phosphate buffer pH 7.5, 50 mM). The reaction was stopped by extracting the mixture with dichloromethane, and the organic phase was dried over anhydrous sodium sulfate.

Enantiomeric purity and conversion were determined by gas chromatography. Enantioselectivity of the variant enzymes was calculated according to Chen et al. (C. S. Chen, Y. Fujimoto, G. Girdaukas, C. J. Sih, J. Am. Chem. Soc. 1982, 104, 7294.).

For a more detailed description of the synthesis of the substrates and the retention times in GC analysis, see Musidlowska-Persson, A. and Bornscheuer, U. T., "Substrate Specificity of the γ-isoenzyme of recombinant pig liver esterase towards acetates of secondary alcohols" J. Mol. Catal. B. Enzym. 2002, 19-20, 129-133.

Stereoselectivity of the Enzymatic Hydrolysis of cis-3,5-diacetoxycyclopent-1-ene The experimental procedure was identical to the resolution of the racemates of secondary alcohols, using 0.5 units (pNPA) of PLE crude extract in 1 ml of reaction mixture containing 10 mM substrate in sodium phosphate buffer pH 7.5 50 mM. The reaction was carried out at 37° C., and samples were taken at the times indicated. Conversion and product enantiomeric excesses were analyzed by gas chromatography. The analysis employed a Hydrodex®-b-3P (heptakis-(2,6-di-O-methyl-3-O-pentyl-b-cyclodextrin) (25 m, 0.25 mm)) GC column (Machery Nagel, Düren, Germany) in a C-R5A Chromatopac/Integrator GC instrument (Shimadzu, Duisburg, Germany). The retention times for isothermal fractionation at a column temperature of 110° C. were: cis-3,5-diacetoxy-cyclopent-1-ene: 21.8 min, 3(S)-acetoxy-5(R)-hydroxy-cyclopent-1-ene: 18.2 min, 3(R)-acetoxy-5(S)-hydroxy-cyclopent-1-ene: 16.0 min.

Results:
Isolation of mRNA from Pig Liver and RT-PCR

The quality of the isolated RNA was checked on an agarose gel (figure not shown), and said RNA was quantified by spectrophotometry (2.6 µg/µl); thus, 260 µg of RNA were obtained from 0.1 g of tissue used. After transcription into cDNA by RT-PCR, the quality of said cDNA was checked by using it as template for amplification of the household gene β-actin. FIG. 1 indicates that the cDNA allowed amplification of the β-actin gene, and its quality is therefore suitable for further experiments.

FIG. 1: cDNA quality control by amplification of the β-actin gene. Templates: lane 1: human cDNA (positive control), lane 2: cDNA from pig liver, lane 3: water (negative control).

Amplification and Cloning of PLE Genes

The cDNA was used for the amplification of PLE genes, using primers based on the sequence of γPLE. As FIG. 2 indicates, application of the reaction mixture after PCR to an agarose gel produced a sharp band at about 1.7 kbp, corresponding to the size of γPLE. This band was excised, the DNA was isolated and cloned into a TOPO vector with the aid of the CACC overhang attached via the forward primer. Recombinant clones were obtained after transforming E. coli Top10 cells with this construct mixture. Plasmid DNA was isolated from these clones, checked by restriction mapping and sequenced.

Figure 2:
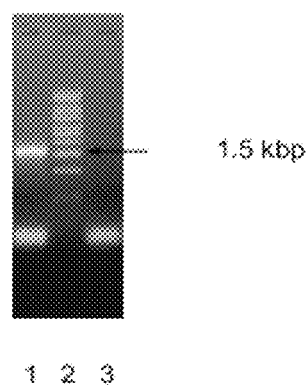
FIG. 2: Amplification of PLE genes from pig liver cDNA. Lane 1: cDNA as template, lane 2: 1 kbp marker, lane 3: water as template (negative control).

FIG. 2: Amplification of PLE genes from pig liver cDNA. Lane 1: cDNA as template, lane 2: 1 kbp marker, lane 3: water as template (negative control).

Sequencing Results

Sequencing of the new PLE genes revealed that four new gene sequences were obtained which are distinct with respect to each other and with respect to γ-PLE. The sites deviating from the γ-PLE sequence are depicted in the alignment of amino acid sequences of FIG. 3. The PLEs and their genes thus present were numbered from 1 to 5, with PLE 1 corresponding to the γ-PLE disclosed previously. The deviations of the new PLEs from the known γ-PLE can be summarized as follows:

PLE 2: 6 Nucleotide substitutions (3 amino acid substitutions) [isoenzyme 4]
PLE 3: 35 Nucleotide substitutions (20 amino acid substitutions) [isoenzyme 24]
PLE 4: 34 Nucleotide substitutions (20 amino acid substitutions) [isoenzyme 39]
PLE 5: 34 Nucleotide substitutions (21 amino acid substitutions) [isoenzyme 41]

Figure 3:
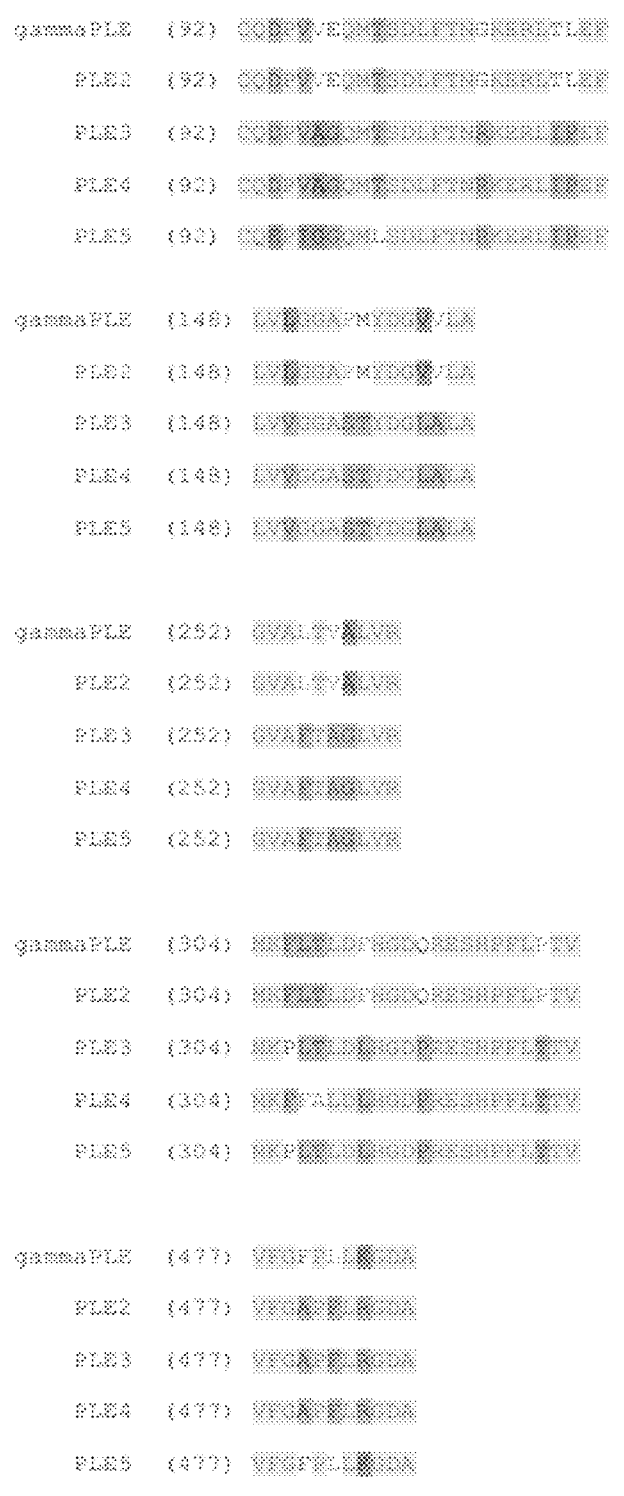

FIG. 3: Partial alignment of the amino acid sequences of the PLEs found, PLEs 2, 3, 4 and 5, with the sequence of γ-PLE (PLE 1).

Expression of the Proteins

The five genes found were subcloned into a pET15b vector. E. coli Origami was transformed with these constructs and with the pGro7 plasmid which codes for the two chaperone parts, GroES and GroEL. Successful overexpression of PLE in E. coli had been described for this expression system (DE 10061864). The strains were cultured on a small scale (50 ml/150 ml), and protein expression of chaperone and PLE construct was induced. In addition, γPLE and *E. coli* Origami with pGro7 without the pET vector were cocultured for comparison and protein expression was induced. The supernatants were disrupted (Volume: 3 ml/9 ml), and the crude extracts containing the soluble intracellular proteins were obtained by centrifugation and used for subsequent experiments.

The protein content in all crude extracts was about 7-9 mg/ml (of which a large part of the protein formed corresponds to the chaperones); the final volume of the crude extract was 3 or 9 ml, depending on the size of the culture.

Native Gel and Fast Red Staining

Figure 4:
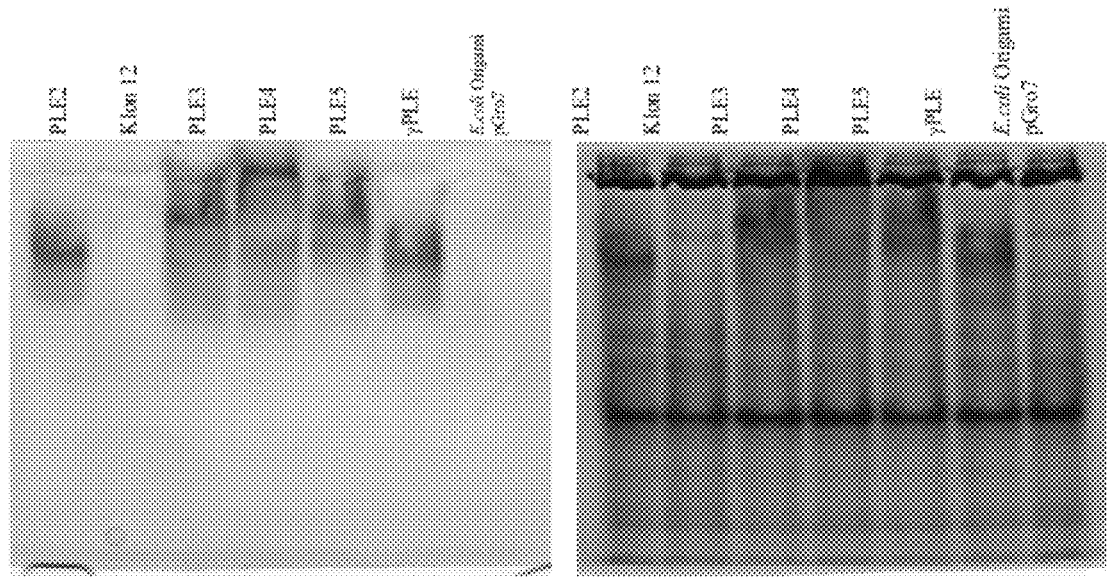
FIG. 4: Native PAGE of the crude extracts of PLE2, clone 12, PLE3, PLE4, PLE5, γPLE and the E. coli Origami pGro7 wild type (negative control). Left-hand side: Fast Red staining with α-naphthyl acetate, right-hand side: subsequent Coomassie Brilliant Blue staining)

Esterase activity was checked by applying the crude extracts to a native gel which was then incubated in Fast Red solution with α-naphthyl acetate as substrate. This was followed by Coomassie staining (FIG. 4: Native PAGE of the crude extracts of PLE2, clone 12, PLE3, PLE4, PLE5, γPLE and the *E. coli* Origami pGro7 wild type (negative control). Left-hand side: Fast Red staining with α-naphthyl acetate, right-hand side: subsequent Coomassie Brilliant Blue staining).

Active esterase bands are visible with PLE2, PLE3, PLE4, PLE5 and γPLE, which strangely have different sizes and are very heavily smeared. This may be due to the method, since native gels do not run as clearly as denaturing SDS gels; however, it is also possible that some crude extracts contain both trimeric and tetrameric PLE constructs, both of which are active.

Clone 12 does not show any activity. Likewise, as expected, no esterase activity is detectable in the crude extract of *E. coli* Origami without the pET15b construct.

The protein bands in Coomassie staining clearly indicate that a lot of chaperone was overexpressed in addition to γPLE. The protein contents determined by means of Bradford thus comprise mainly the chaperone and do not give any information about the γPLE content. The extent of overexpression cannot be assessed precisely anymore on the basis of the Coomassie staining carried out after Fast Red. Compared to the *E. coli* wild type with chaperone there is no additional protein band visible in the region of the active bands. However, frequently the protein can no longer be stained with Coomassie after activity staining. However, it could also mean that overexpression is only very low but still provides protein with good activity.

Activity with p-Nitrophenyl Acetate

Esterase activity was checked first by using the pNPA assay. It produced the results listed in table 1.

TABLE 1

Volume activities (U/ml) of the PLE variants and the expression strain (*E. coli* Origami with chaperone plasmid pGro7) with pNPA. All esterases carry an N-terminal His6 tag.

| Crude extract | Volume activity (U/ml) |
|---|---|
| PLE 1 (γ-PLE) | 11 |
| PLE 2 | 8 |
| PLE 3 | 21 |
| PLE 4 | 26 |
| PLE 5 | 40 |
| *E. coli* Origami + pGro7 | 0.02 |

All PLEs show activity with pNPA, which is for some of the new esterases even twice to four times as high as for γ-PLE.

Activity with Achiral Esters

The activity of the new PLE variants with achiral esters was examined using pH stat. After purification of the enzymes, specific activities were determined which are listed in table 2.

TABLE 2

Specific activities of the new PLEs and γ-PLE with some achiral esters, determined by pH stat at 37° C. and pH 7.5 over a measuring period of 10 min.

| | Tributyrin | Ethyl caprylate | Methyl butyrate | Ethyl acetate | Triolein |
|---|---|---|---|---|---|
| PLE 1 (γ-PLE) | 306 | 63 | 57 | 38 | 0 |
| PLE 3 | 224 | 63 | 23 | 24 | 8 |
| PLE 4 | 131 | 44 | 76 | 25 | 9 |
| PLE 5 | 409 | 144 | 182 | 17 | 12 |

Resolution of the Racemates of Acetates of Secondary Alcohols

Hydrolysis of the following racemic acetates was investigated:

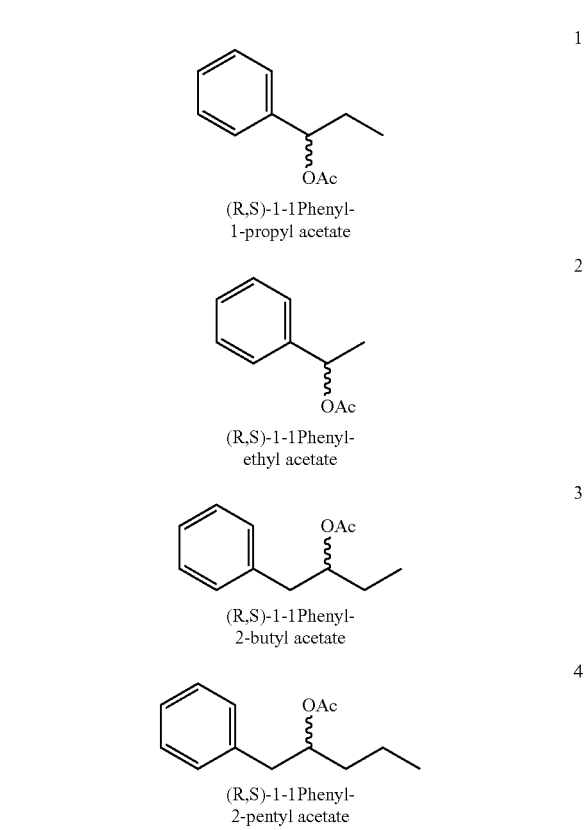

Gas chromatographic studies produced the results depicted in tables 3 to 6. The data obtained for the commercial PLE preparations by A. Musidlowska (Musidlowska-Persson, A. and Bornscheuer, U. T., J. Mol. Catal. B. Enzym. 2002, 19-20, 129-133.) have been added for comparison.

TABLE 3

Enantioselectivity of the new PLE variants in the kinetic resolution of the racemates of 1 (R,S)-1-phenyl-1-propyl acetate.

| PLE isoenzyme | Time [h] | Enantiomeric excess [% ee$_S$] | [% ee$_P$] | Conversion [%] | E | Preference |
|---|---|---|---|---|---|---|
| PLE 1 (γ-PLE) | 4 | 41 | 45 | 48 | 4 | R |
| PLE 2 | 2 | 38 | 49 | 44 | 4 | R |
| PLE 3 | 1 | 25 | 34 | 43 | 3 | S |
| PLE 4 | 1.5 | 51 | 71 | 42 | 10 | R |
| PLE 5 | 1 | 61 | 93 | 40 | 51 | R |
| Fluka PLE (*) | 1 | 21 | 28 | 43 | 2.2 | R |
| Chirazyme E2 (*) | 0.5 | 18 | 27 | 40 | 2.1 | R |

(*) Data for Fluka PLE and Chirazyme E2 were taken from Musidlowska-Persson, A. and Bornscheuer, U. T., J. Mol. Catal. B. Enzym. 2002, 19-20, 129-133.

TABLE 4

Enantioselectivity of the new PLE variants in the kinetic resolution of the racemates of 2 (R,S)-1-phenyl-ethyl acetate.

| PLE isoenzyme | Time [h] | Enantiomeric excess [% ee$_S$] | [% ee$_P$] | Conversion [%] | E | Preference |
|---|---|---|---|---|---|---|
| PLE 1 (γ-PLE) | 2 | 74 | 77 | 49 | 17 | R |
| PLE 2 | 2 | 67 | 81 | 45 | 19 | R |
| PLE 3 | 1.5 | 18 | 24 | 43 | 2 | S |
| PLE 4 | 3 | 68 | 94 | 42 | 66 | R |
| PLE 5 | 2 | 79 | 95 | 45 | 94 | R |
| Fluka PLE (*) | 1.5 | 65 | 56 | 54 | 7 | R |
| Chirazyme E2 (*) | 1 | 61 | 56 | 52 | 7 | R |

(*) Data for Fluka PLE and Chirazyme E2 were taken from Musidlowska-Persson, A. and Bornscheuer, U. T., J. Mol. Catal. B. Enzym. 2002, 19-20, 129-133.

TABLE 5

Enantioselectivity of the new PLE variants in the kinetic resolution of the racemates of 3 (R,S)-1-phenyl-2-butyl acetate.

| PLE isoenzyme | Time [h] | Enantiomeric excess [% ee$_S$] | [% ee$_P$] | Conversion [%] | E | Preference |
|---|---|---|---|---|---|---|
| PLE 1 (γ-PLE) | 4 | 83 | 93 | 47 | 72 | S |
| PLE 2 | 4 | 67 | 93 | 42 | 55 | S |
| PLE 3 | 4 | 26 | 32 | 45 | 2 | R |
| PLE 4 | 3 | 65 | 83 | 43 | 25 | R |
| PLE 5 | 4 | 82 | 89 | 48 | 45 | R |
| Fluka PLE (*) | 2 | 12 | 12 | 49 | 1.4 | S |
| Chirazyme E2 (*) | 1 | 58 | 40 | 59 | 4 | S |

(*) Data for Fluka PLE and Chirazyme E2 were taken from Musidlowska-Persson, A. and Bornscheuer, U. T., J. Mol. Catal. B. Enzym. 2002, 19-20, 129-133.

TABLE 6

Enantioselectivity of the new PLE variants in the kinetic resolution of the racemates of 4 (R,S)-1-phenyl-2-pentyl acetate.

| PLE isoenzyme | Time [h] | Enantiomeric excess [% ee$_S$] | [% ee$_P$] | Conversion [%] | E | Preference |
|---|---|---|---|---|---|---|
| PLE 1 (γ-PLE) (*) | 2 | 69 | 78 | 47 | 17 | S |
| PLE 2 | 0.2 | 71 | 87 | 45 | 30 | S |
| PLE 3 | 0.05 | 23 | 37 | 38 | 3 | R |
| PLE 4 | 0.2 | 76 | 84 | 48 | 27 | R |
| PLE 5 | 0.5 | 86 | 85 | 50 | 34 | R |
| Fluka PLE (*) | 0.3 | 24 | 26 | 48 | 2.1 | S |
| Chirazyme E2 (*) | 0.3 | 21 | 24 | 46 | 2 | S |

(*) Data for Fluka PLE and Chirazyme E2 were taken from Musidlowska-Persson, A. and Bornscheuer, U. T., J. Mol. Catal. B. Enzym. 2002, 19-20, 129-133.

Figure 5:
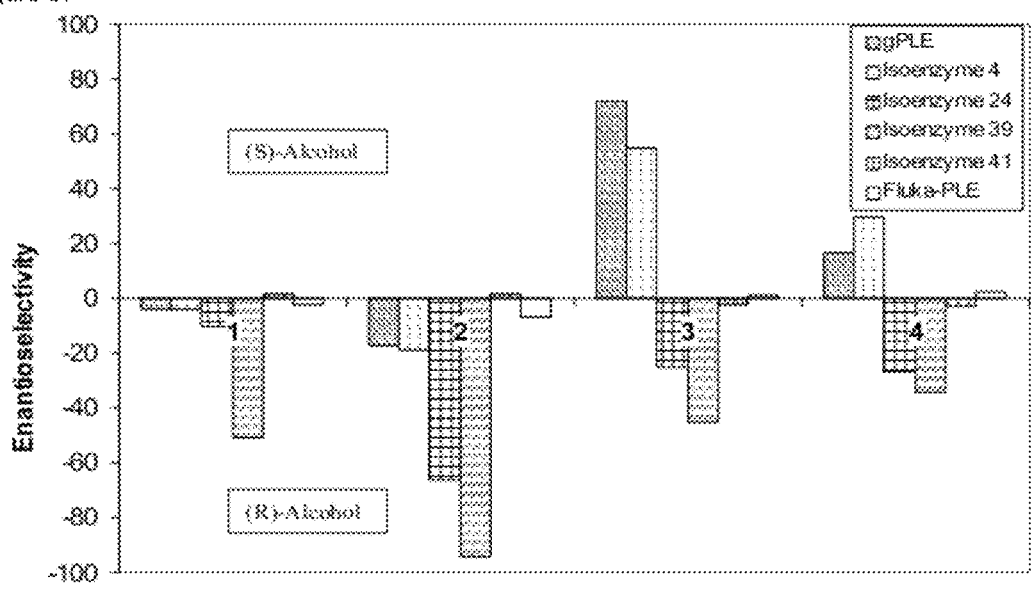
FIG. 5: Enantioselectivities of various pig liver esterase isoenzymes in the kinetic resolution of the racemates of substrates 1-4. The data of the commercial Fluka PLE were taken from the literature (Musidlowska-Persson, A. and Bornscheuer, U.T., J. Mol. Catal. B. Enzym. 2002, 19-20, 129-133).

FIG. 5 illustrates the differences in the enantiomeric excesses again diagrammatically.

FIG. 5. Enantioselectivities of various pig liver esterase isoenzymes in the kinetic resolution of the racemates of substrates 1-4. The data of the commercial Fluka PLE were taken from the literature (Musidlowska-Persson, A. and Bornscheuer, U. T., J. Mol. Catal. B. Enzym. 2002, 19-20, 129-133).

Hydrolysis of cis-3,5-diacetoxycyclopent-1-ene

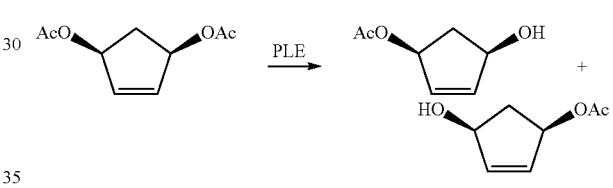

TABLE 7

Asymmetrization of meso-cis-3,5-diacetoxycyclopent-1-ene by the new PLE variants, γ-PLE (PLE 1) and the commercially available Fluka PLE. The reaction was carried out with 0.5 units (pNPA) of crude extract at 37° C., and enantiomeric excesses were determined by gas chromatography.

| PLE isoenzyme | Time [h] | Enantiomeric excess [% ee$_P$] | Conversion [%] | Preference |
|---|---|---|---|---|
| PLE 1 | 14 | 82 | 96 | 6a (3S,5R) |
| PLE 2 | 14 | 83 | 91 | 6a (3S,5R) |
| PLE 3 | 14 | 83 | 99 | 6a (3S,5R) |
| PLE 4 | 14 | 42 | 95 | 6b (3R,5S) |
| PLE 5 | 14 | 17 | 100 | 6b (3R,5S) |
| Fluka PLE | 20 | 61 | 100 | 6a (3S,5R) |

Figure 6:
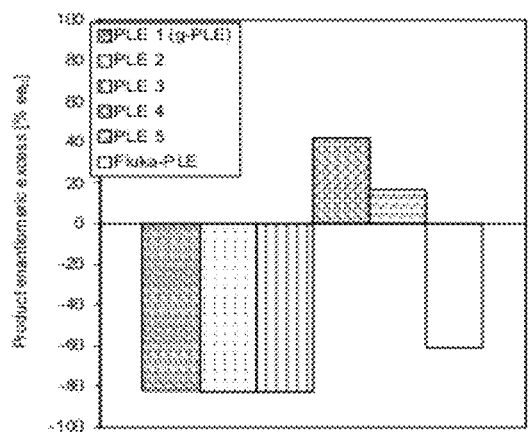
FIG. 6: Product enantiomeric excess of various pig liver esterase isoenzymes in the hydrolysis of cis-3,5-diacetoxycyclopent-1-ene.

FIG. 6 illustrates the differences of the PLE variants with respect to product enantiomeric excesses.

FIG. 6. Product enantiomeric excess of various pig liver esterase isoenzymes in the hydrolysis of cis-3,5-diacetoxy-cyclopent-1-ene.

Influence of Inhibitors

The inhibitability of the new PLE variants was determined by treating the crude extracts with any of three esterase inhibitors. The influence of phenylmethylsulfonyl fluoride, sodium fluoride and physostigmine was investigated. Samples were taken at certain points in time and the remaining esterase activity was determined by the pNPA assay. Table 8 depicts the results.

TABLE 8

Remaining activities [%] of the new PLE isoenzymes after incubation with the three inhibitors sodium fluoride, phenylmethylsulfonyl fluoride and physostigmine at 25° C. The activities were determined by the pNPA assay.

| Inhibitor | Concentration | PLE 1 (γ-PLE) | PLE 2 | PLE 3 | PLE 4 | PLE 5 |
|---|---|---|---|---|---|---|
| NaF | 1 mM | | | | | |
| 5 min | | 20 | 17 | 44 | 64 | 83 |
| 30 min | | 21 | 15 | 46 | 66 | 88 |
| Phenylmethylsulfonyl fluoride (PMSF) | 0.01 mM | | | | | |
| 1 min | | 97 | 87 | 77 | 78 | 88 |
| 5 min | | 85 | 82 | 51 | 56 | 76 |
| 30 min | | 55 | 50 | 7 | 7 | 24 |
| 60 min | | 46 | 36 | 5 | 2 | 3 |
| Physostigmine | 0.01 mM | | | | | |
| 1 min | | 41 | 61 | 83 | 90 | 94 |
| 5 min | | 12 | 25 | 81 | 82 | 98 |
| 30 min | | 7 | 6 | 72 | 66 | 75 |

The invention claimed is:

1. An isolated polypeptide having esterase activity, wherein said polypeptide comprises the amino acid sequence of SEQ ID NO:2, except for the alternative amino acid R at position 108, and wherein said polypeptide optionally also comprises one or more additional alternative amino acids selected from the group consisting of:

| Position | Alternative Amino acid |
|---|---|
| 94 | E |
| 96 | I |
| 97 | A, G |
| 98 | G |
| 101 | L |
| 108 | R |
| 113 | I |
| 114 | P |
| 150 | V |
| 154 | S |
| 155 | T |
| 159 | L |
| 160 | A |

-continued

| Position | Alternative Amino acid |
|---|---|
| 255 | F |
| 257 | A |
| 258 | G |
| 306 | P |
| 307 | F |
| 308 | A |
| 311 | L |
| 315 | P |
| 323 | T |
| 480 | A |
| 482 | F |
| 484 | R. |

2. The polypeptide of claim 1, wherein, except for R at position 108 and said one or more additional alternative amino acids that are optionally present, said polypeptide consists of the amino acid sequence of SEQ ID NO:2.

3. The polypeptide of claim 1, wherein, besides R at position 108, said polypeptide's amino acid sequence comprises at least one of said additional alternative amino acids.

4. The polypeptide of claim 1, wherein, besides R at position 108, said polypeptide's amino acid sequence comprises at least two of said additional alternative amino acids.

5. The polypeptide of claim 1, wherein, besides R at position 108, said polypeptide's amino acid sequence comprises at least four of said additional alternative amino acids.

6. The polypeptide of claim 1, wherein, besides R at position 108, said polypeptide's amino acid sequence comprises at least six of said additional alternative amino acids.

7. The polypeptide of claim 1, wherein, besides R at position 108, said polypeptide's amino acid sequence comprises at least eight of said alternative amino acids.

8. The polypeptide of claim 1, wherein, besides R at position 108, said polypeptide's amino acid sequence comprises at least 10 of said alternative amino acids.

9. The polypeptide of claim 1, wherein, besides R at position 108, said polypeptide's amino acid sequence comprises at least fifteen of said alternative amino acids.

10. The polypeptide of claim 1, wherein, besides R at position 108, said polypeptide's amino acid sequence comprises at least one of the following alternative amino acids:

| Position | Alternative Amino acid |
|---|---|
| 101 | L |
| 113 | I |
| 114 | P |
| 150 | V |
| 154 | S |
| 155 | T |
| 159 | L |
| 160 | A |
| 255 | F |
| 257 | A |
| 258 | G |
| 306 | P |
| 323 | T. |

11. The polypeptide of claim 10, wherein, besides R at position 108, said polypeptide's amino acid sequence comprises at least five of said alternative amino acids.

12. The polypeptide of claim 10, wherein, besides R at position 108, said polypeptide's amino acid sequence comprises at least ten of said alternative amino acids.

13. The polypeptide of claim 10, wherein, besides R at position 108, said polypeptide's amino acid sequence comprises all of said alternative amino acids.

14. The polypeptide of claim 1, wherein said polypeptide comprises the amino acid sequence of SEQ ID NO:6.

15. The polypeptide of claim 1, wherein said polypeptide consists of the amino acid sequence of SEQ ID NO:6.

16. The polypeptide of claim 1, wherein said polypeptide comprises the amino acid sequence of SEQ ID NO:8.

17. The polypeptide of claim 1, wherein said polypeptide consists of the amino acid sequence of SEQ ID NO:8.

18. The polypeptide of claim 1, wherein said polypeptide comprises the amino acid sequence of SEQ ID NO:10.

19. The polypeptide of claim 1, wherein said polypeptide consists of the amino acid sequence of SEQ ID NO:10.

* * * * *

SEQUENCE LISTING

```
<160> NUMBER OF SEQ ID NOS: 12

<210> SEQ ID NO 1
<211> LENGTH: 1698
<212> TYPE: DNA
<213> ORGANISM: Pig liver
<220> FEATURE:
<221> NAME/KEY: CDS
<222> LOCATION: (1)..(1698)

<400> SEQUENCE: 1 atg ggc agc agc cat cat cat cat cat cac agc agc ggc ctg gtg ccg      48
Met Gly Ser Ser His His His His His His Ser Ser Gly Leu Val Pro
1               5                   10                  15 cgc ggc agc cat atg ggg cag cca gcc tcg ccg cct gtt gtg gac act      96
Arg Gly Ser His Met Gly Gln Pro Ala Ser Pro Pro Val Val Asp Thr
                20                  25                  30 gcc cag ggc cga gtc ctg ggg aag tac gtc agc tta gaa ggc ctg gca     144
Ala Gln Gly Arg Val Leu Gly Lys Tyr Val Ser Leu Glu Gly Leu Ala
            35                  40                  45 cag ccg gtg gcc gtc ttc ctg gga gtc cct ttt gcc aag ccc cct ctc     192
Gln Pro Val Ala Val Phe Leu Gly Val Pro Phe Ala Lys Pro Pro Leu
        50                  55                  60 gga tcc ttg agg ttt gct ccg ccg cag cct gca gaa cca tgg agc ttc     240
Gly Ser Leu Arg Phe Ala Pro Pro Gln Pro Ala Glu Pro Trp Ser Phe
65                  70                  75                  80 gtg aag aac acc acc tcc tac cct ccc atg tgc tgc cag gac cca gta     288
Val Lys Asn Thr Thr Ser Tyr Pro Pro Met Cys Cys Gln Asp Pro Val
                85                  90                  95 gtg gag cag atg acc tca gat cta ttt acc aac gga aag gag agg ctc     336
Val Glu Gln Met Thr Ser Asp Leu Phe Thr Asn Gly Lys Glu Arg Leu
                100                 105                 110 act ctg gag ttt tct gaa gac tgt ctc tac cta aat att tac acc cct     384
Thr Leu Glu Phe Ser Glu Asp Cys Leu Tyr Leu Asn Ile Tyr Thr Pro
            115                 120                 125 gct gac ctg aca aag agg ggc aga ctg ccg gtg atg gtg tgg atc cac     432
Ala Asp Leu Thr Lys Arg Gly Arg Leu Pro Val Met Val Trp Ile His
        130                 135                 140 gga gga ggc ctg gtg ttg ggc ggg gca cca atg tat gat ggg gtg gtg     480
Gly Gly Gly Leu Val Leu Gly Gly Ala Pro Met Tyr Asp Gly Val Val
145                 150                 155                 160 ctt gct gcg cat gaa aac gtg gtg gtg gcc atc cag tac cgc ctg         528
Leu Ala Ala His Glu Asn Val Val Val Ala Ile Gln Tyr Arg Leu
                165                 170                 175
```

```
-continued ggc atc tgg gga ttc ttc agc aca ggg gat gaa cac agc cgg ggc aac      576
Gly Ile Trp Gly Phe Phe Ser Thr Gly Asp Glu His Ser Arg Gly Asn
        180                 185                 190 tgg ggt cac ttg gac cag gtg gcc gca ctg cac tgg gtc cag gag aac      624
Trp Gly His Leu Asp Gln Val Ala Ala Leu His Trp Val Gln Glu Asn
                195                 200                 205 atc gcc aac ttt gga ggc gac cca ggc tct gtg acc atc ttt gga gag      672
Ile Ala Asn Phe Gly Gly Asp Pro Gly Ser Val Thr Ile Phe Gly Glu
    210                 215                 220 tca gca gga ggg gaa agt gtc tct gtt ctg gtg ttg tct ccc ttg gcc      720
Ser Ala Gly Gly Glu Ser Val Ser Val Leu Val Leu Ser Pro Leu Ala
225                 230                 235                 240 aag aac ctc ttc cac cgg gcc atc tct gag agt ggc gtg gcc ctc act      768
Lys Asn Leu Phe His Arg Ala Ile Ser Glu Ser Gly Val Ala Leu Thr
                245                 250                 255 gtt gcc ctg gtc agg aag gac atg aag gct gca gct aag caa att gct      816
Val Ala Leu Val Arg Lys Asp Met Lys Ala Ala Ala Lys Gln Ile Ala
            260                 265                 270 gtc ctt gct ggg tgt aaa acc acc acc tcg gct gtc ttt gtt cac tgc      864
Val Leu Ala Gly Cys Lys Thr Thr Thr Ser Ala Val Phe Val His Cys
        275                 280                 285 ctg cgc cag aag tcg gag gac gag ctc ttg gac tta acg ctg aag atg      912
Leu Arg Gln Lys Ser Glu Asp Glu Leu Leu Asp Leu Thr Leu Lys Met
    290                 295                 300 aaa ttt tta act ctt gat ttt cat gga gac caa aga gag agc cat ccc      960
Lys Phe Leu Thr Leu Asp Phe His Gly Asp Gln Arg Glu Ser His Pro
305                 310                 315                 320 ttc ctg ccc act gtg gtg gat gga gtg ctg ctg ccc aag atg cct gaa     1008
Phe Leu Pro Thr Val Val Asp Gly Val Leu Leu Pro Lys Met Pro Glu
                325                 330                 335 gag att ctg gct gag aag gat ttc aac act gtc ccc tac atc gtg gga     1056
Glu Ile Leu Ala Glu Lys Asp Phe Asn Thr Val Pro Tyr Ile Val Gly
            340                 345                 350 atc aac aag caa gag ttt ggc tgg ctt ctg cca acg atg atg ggc ttc     1104
Ile Asn Lys Gln Glu Phe Gly Trp Leu Leu Pro Thr Met Met Gly Phe
        355                 360                 365 ccc ctc tct gaa ggc aag ctg gac cag aag acg gcc acg tca ctc ctg     1152
Pro Leu Ser Glu Gly Lys Leu Asp Gln Lys Thr Ala Thr Ser Leu Leu
    370                 375                 380 tgg aag tcc tac ccc atc gct aac atc cct gag gaa ctg act cca gtg     1200
Trp Lys Ser Tyr Pro Ile Ala Asn Ile Pro Glu Glu Leu Thr Pro Val
385                 390                 395                 400 gcc act gac aag tat ttg ggg ggg aca gac gac ccc gtc aaa aag aaa     1248
Ala Thr Asp Lys Tyr Leu Gly Gly Thr Asp Asp Pro Val Lys Lys Lys
                405                 410                 415 gac ctg ttc ctg gac ttg atg ggg gat gtg gtg ttt ggt gtc cca tct     1296
Asp Leu Phe Leu Asp Leu Met Gly Asp Val Val Phe Gly Val Pro Ser
            420                 425                 430 gtg acg gtg gcc cgt caa cac aga gat gca gga gcc ccc acc tac atg     1344
Val Thr Val Ala Arg Gln His Arg Asp Ala Gly Ala Pro Thr Tyr Met
        435                 440                 445 tat gag ttt cag tat cgc cca agc ttc tca tcg gac aag aaa ccc aag     1392
Tyr Glu Phe Gln Tyr Arg Pro Ser Phe Ser Ser Asp Lys Lys Pro Lys
    450                 455                 460 acg gtg atc ggg gac cac ggg gat gag atc ttc tcc gtc ttt ggt ttt     1440
Thr Val Ile Gly Asp His Gly Asp Glu Ile Phe Ser Val Phe Gly Phe
465                 470                 475                 480 cca ctg tta aaa ggc gat gcc cca gaa gag gag gtc agt ctc agc aag     1488
Pro Leu Leu Lys Gly Asp Ala Pro Glu Glu Glu Val Ser Leu Ser Lys
                485                 490                 495
```

```
acg gtg atg aaa ttc tgg gcc aac ttt gct cgc agt ggg aac ccc aat    1536
Thr Val Met Lys Phe Trp Ala Asn Phe Ala Arg Ser Gly Asn Pro Asn
        500                 505                 510 ggg gag ggg ctg ccc cat tgg ccg atg tac gac cag gaa gaa ggg tac    1584
Gly Glu Gly Leu Pro His Trp Pro Met Tyr Asp Gln Glu Glu Gly Tyr
    515                 520                 525 ctt cag atc ggc gtc aac acc cag gca gcc aag agg ctg aaa ggt gaa    1632
Leu Gln Ile Gly Val Asn Thr Gln Ala Ala Lys Arg Leu Lys Gly Glu
530                 535                 540 gaa gtg gcc ttc tgg aac gat ctc ctg tcc aag gag gca gca aag aag    1680
Glu Val Ala Phe Trp Asn Asp Leu Leu Ser Lys Glu Ala Ala Lys Lys
545                 550                 555                 560 cca ccc aag ata aag tga                                            1698
Pro Pro Lys Ile Lys
                565
```

<210> SEQ ID NO 2
<211> LENGTH: 565
<212> TYPE: PRT
<213> ORGANISM: Pig liver

<400> SEQUENCE: 2

```
Met Gly Ser Ser His His His His His His Ser Ser Gly Leu Val Pro
1               5                   10                  15

Arg Gly Ser His Met Gly Gln Pro Ala Ser Pro Val Val Asp Thr
            20                  25                  30

Ala Gln Gly Arg Val Leu Gly Lys Tyr Val Ser Leu Glu Gly Leu Ala
            35                  40                  45

Gln Pro Val Ala Val Phe Leu Gly Val Pro Phe Ala Lys Pro Pro Leu
    50                  55                  60

Gly Ser Leu Arg Phe Ala Pro Pro Gln Pro Ala Glu Pro Trp Ser Phe
65                  70                  75                  80

Val Lys Asn Thr Thr Ser Tyr Pro Pro Met Cys Cys Gln Asp Pro Val
                85                  90                  95

Val Glu Gln Met Thr Ser Asp Leu Phe Thr Asn Gly Lys Glu Arg Leu
            100                 105                 110

Thr Leu Glu Phe Ser Glu Asp Cys Leu Tyr Leu Asn Ile Tyr Thr Pro
        115                 120                 125

Ala Asp Leu Thr Lys Arg Gly Arg Leu Pro Val Met Val Trp Ile His
    130                 135                 140

Gly Gly Gly Leu Val Leu Gly Ala Pro Met Tyr Asp Gly Val Val
145                 150                 155                 160

Leu Ala Ala His Glu Asn Val Val Val Ala Ile Gln Tyr Arg Leu
                165                 170                 175

Gly Ile Trp Gly Phe Phe Ser Thr Gly Asp Glu His Ser Arg Gly Asn
            180                 185                 190

Trp Gly His Leu Asp Gln Val Ala Ala Leu His Trp Val Gln Glu Asn
        195                 200                 205

Ile Ala Asn Phe Gly Gly Asp Pro Gly Ser Val Thr Ile Phe Gly Glu
    210                 215                 220

Ser Ala Gly Gly Glu Ser Val Ser Val Leu Val Leu Ser Pro Leu Ala
225                 230                 235                 240

Lys Asn Leu Phe His Arg Ala Ile Ser Glu Ser Gly Val Ala Leu Thr
                245                 250                 255

Val Ala Leu Val Arg Lys Asp Met Lys Ala Ala Lys Gln Ile Ala
            260                 265                 270
```

```
Val Leu Ala Gly Cys Lys Thr Thr Ser Ala Val Phe Val His Cys
        275                 280                 285

Leu Arg Gln Lys Ser Glu Asp Glu Leu Leu Asp Leu Thr Leu Lys Met
    290                 295                 300

Lys Phe Leu Thr Leu Asp Phe His Gly Asp Gln Arg Glu Ser His Pro
305                 310                 315                 320

Phe Leu Pro Thr Val Val Asp Gly Val Leu Leu Pro Lys Met Pro Glu
                325                 330                 335

Glu Ile Leu Ala Glu Lys Asp Phe Asn Thr Val Pro Tyr Ile Val Gly
            340                 345                 350

Ile Asn Lys Gln Glu Phe Gly Trp Leu Leu Pro Thr Met Met Gly Phe
        355                 360                 365

Pro Leu Ser Glu Gly Lys Leu Asp Gln Lys Thr Ala Thr Ser Leu Leu
    370                 375                 380

Trp Lys Ser Tyr Pro Ile Ala Asn Ile Pro Glu Glu Leu Thr Pro Val
385                 390                 395                 400

Ala Thr Asp Lys Tyr Leu Gly Gly Thr Asp Asp Pro Val Lys Lys Lys
                405                 410                 415

Asp Leu Phe Leu Asp Leu Met Gly Asp Val Val Phe Gly Val Pro Ser
            420                 425                 430

Val Thr Val Ala Arg Gln His Arg Asp Ala Gly Ala Pro Thr Tyr Met
        435                 440                 445

Tyr Glu Phe Gln Tyr Arg Pro Ser Phe Ser Ser Asp Lys Lys Pro Lys
    450                 455                 460

Thr Val Ile Gly Asp His Gly Asp Glu Ile Phe Ser Val Phe Gly Phe
465                 470                 475                 480

Pro Leu Leu Lys Gly Asp Ala Pro Glu Glu Val Ser Leu Ser Lys
                485                 490                 495

Thr Val Met Lys Phe Trp Ala Asn Phe Ala Arg Ser Gly Asn Pro Asn
            500                 505                 510

Gly Glu Gly Leu Pro His Trp Pro Met Tyr Asp Gln Glu Glu Gly Tyr
        515                 520                 525

Leu Gln Ile Gly Val Asn Thr Gln Ala Ala Lys Arg Leu Lys Gly Glu
    530                 535                 540

Glu Val Ala Phe Trp Asn Asp Leu Leu Ser Lys Glu Ala Ala Lys Lys
545                 550                 555                 560

Pro Pro Lys Ile Lys
                565

<210> SEQ ID NO 3
<211> LENGTH: 1698
<212> TYPE: DNA
<213> ORGANISM: Artificial
<220> FEATURE:
<223> OTHER INFORMATION: PLE mutant
<220> FEATURE:
<221> NAME/KEY: CDS
<222> LOCATION: (1)..(1698)

<400> SEQUENCE: 3 atg ggc agc agc cat cat cat cat cat cac agc agc ggc ctg gtg ccg      48
Met Gly Ser Ser His His His His His His Ser Ser Gly Leu Val Pro
1               5                  10                  15 cgc ggc agc cat atg ggg cag cca gcc tcg ccg cct gtt gtg gac act      96
Arg Gly Ser His Met Gly Gln Pro Ala Ser Pro Pro Val Val Asp Thr
            20                  25                  30 gcc cag ggc cga gtc ctg ggg aag tac gtc agc tta gaa ggc ctg gca     144
Ala Gln Gly Arg Val Leu Gly Lys Tyr Val Ser Leu Glu Gly Leu Ala
```

-continued

|  |  |  |  | 35 |  |  |  | 40 |  |  |  | 45 |  |  |  |  |
|---|---|---|---|---|---|---|---|---|---|---|---|---|---|---|---|---|

```
cag ccg gtg gcc gtc ttc ctg gga gtc cct ttt gcc aag ccc cct ctc       192
Gln Pro Val Ala Val Phe Leu Gly Val Pro Phe Ala Lys Pro Pro Leu
     50                  55                  60 gga tcc ttg agg ttt gct ccg ccg cag cct gca gaa cca tgg agc ttc       240
Gly Ser Leu Arg Phe Ala Pro Pro Gln Pro Ala Glu Pro Trp Ser Phe
 65              70                  75                  80 gtg aag aac acc acc tcc tac cct ccc atg tgc tgc cag gac cca gta       288
Val Lys Asn Thr Thr Ser Tyr Pro Pro Met Cys Cys Gln Asp Pro Val
                 85                  90                  95 gtg gag cag atg acc tca gat cta ttt acc aac gga aag gag agg ctc       336
Val Glu Gln Met Thr Ser Asp Leu Phe Thr Asn Gly Lys Glu Arg Leu
            100                 105                 110 act ctg gag ttt tct gaa gac tgt ctc tac cta aat att tac acc cct       384
Thr Leu Glu Phe Ser Glu Asp Cys Leu Tyr Leu Asn Ile Tyr Thr Pro
        115                 120                 125 gct gac ctg aca aag agg ggc aga ctg ccg gtg atg gtg tgg atc cac       432
Ala Asp Leu Thr Lys Arg Gly Arg Leu Pro Val Met Val Trp Ile His
    130                 135                 140 gga gga ggc ctg gtg ttg ggc ggg gca cca atg tat gat ggg gtg gtg       480
Gly Gly Gly Leu Val Leu Gly Gly Ala Pro Met Tyr Asp Gly Val Val
145                 150                 155                 160 ctt gct gcg cat gaa aac gtg gtg gtg gtg gcc atc cag tac cgc ctg       528
Leu Ala Ala His Glu Asn Val Val Val Val Ala Ile Gln Tyr Arg Leu
                165                 170                 175 ggc atc tgg gga ttc ttc agc aca ggg gat gaa cac agc cgg ggc aac       576
Gly Ile Trp Gly Phe Phe Ser Thr Gly Asp Glu His Ser Arg Gly Asn
            180                 185                 190 tgg ggt cac ttg gac cag gtg gcc gca ctg cac tgg gtc cag gag aac       624
Trp Gly His Leu Asp Gln Val Ala Ala Leu His Trp Val Gln Glu Asn
        195                 200                 205 atc gcc aac ttt gga ggc gac cca ggc tct gtg acc atc ttt gga gag       672
Ile Ala Asn Phe Gly Gly Asp Pro Gly Ser Val Thr Ile Phe Gly Glu
    210                 215                 220 tca gca gga ggg gaa agt gtc tct gtt ctg gtg ttg tct ccc ttg gcc       720
Ser Ala Gly Gly Glu Ser Val Ser Val Leu Val Leu Ser Pro Leu Ala
225                 230                 235                 240 aag aac ctc ttc cac cgg gcc atc tct gag agt ggc gtg gcc ctc act       768
Lys Asn Leu Phe His Arg Ala Ile Ser Glu Ser Gly Val Ala Leu Thr
                245                 250                 255 gtt gcc ctg gtc agg aag gac atg aag gct gca gct aag caa att gct       816
Val Ala Leu Val Arg Lys Asp Met Lys Ala Ala Ala Lys Gln Ile Ala
            260                 265                 270 gtc ctt gct ggg tgt aaa acc acc acc tcg gct gtc ttt gtt cac tgc       864
Val Leu Ala Gly Cys Lys Thr Thr Thr Ser Ala Val Phe Val His Cys
        275                 280                 285 ctg cgc cag aag tcg gag gac gag ctc ttg gac tta acg ctg aag atg       912
Leu Arg Gln Lys Ser Glu Asp Glu Leu Leu Asp Leu Thr Leu Lys Met
    290                 295                 300 aaa ttt tta act ctt gat ttt cat gga gac caa aga gag agc cat ccc       960
Lys Phe Leu Thr Leu Asp Phe His Gly Asp Gln Arg Glu Ser His Pro
305                 310                 315                 320 ttc ctg ccc act gtg gtg gat gga gtg ctg ctg ccc aag atg cct gaa      1008
Phe Leu Pro Thr Val Val Asp Gly Val Leu Leu Pro Lys Met Pro Glu
                325                 330                 335 gag att ctg gct gag aag gat ttc aac act gtc ccc tac atc gtg gga      1056
Glu Ile Leu Ala Glu Lys Asp Phe Asn Thr Val Pro Tyr Ile Val Gly
            340                 345                 350 atc aac aag caa gag ttt ggc tgg ctt ctg cca acg atg atg ggc ttc      1104
Ile Asn Lys Gln Glu Phe Gly Trp Leu Leu Pro Thr Met Met Gly Phe
```

```
ccc ctc tct gaa ggc aag ctg gac cag aag acg gcc acg tca ctc ctg      1152
Pro Leu Ser Glu Gly Lys Leu Asp Gln Lys Thr Ala Thr Ser Leu Leu
    370                 375                 380 tgg aag tcc tac ccc atc gct aac atc cct gag gaa ctg act cca gtg      1200
Trp Lys Ser Tyr Pro Ile Ala Asn Ile Pro Glu Glu Leu Thr Pro Val
385                 390                 395                 400 gcc act gac aag tat ttg ggg ggg aca gac gac ccc gtc aaa aag aaa      1248
Ala Thr Asp Lys Tyr Leu Gly Gly Thr Asp Asp Pro Val Lys Lys Lys
                405                 410                 415 gac ctg ttc ctg gac ttg atg ggg gat gtg gtg ttt ggt gtc cca tct      1296
Asp Leu Phe Leu Asp Leu Met Gly Asp Val Val Phe Gly Val Pro Ser
        420                 425                 430 gtg acg gtg gcc cgt caa cac aga gat gca gga gcc ccc acc tac atg      1344
Val Thr Val Ala Arg Gln His Arg Asp Ala Gly Ala Pro Thr Tyr Met
                435                 440                 445 tat gag ttt cag tat cgc cca agc ttc tca tcg gac aag aaa ccc aag      1392
Tyr Glu Phe Gln Tyr Arg Pro Ser Phe Ser Ser Asp Lys Lys Pro Lys
    450                 455                 460 acg gtg atc ggg gac cac ggg gat gag atc ttc tcc gtc ttt ggg gct      1440
Thr Val Ile Gly Asp His Gly Asp Glu Ile Phe Ser Val Phe Gly Ala
465                 470                 475                 480 cca ttt tta aga ggc gat gcc cca gaa gag gag gtc agt ctc agc aag      1488
Pro Phe Leu Arg Gly Asp Ala Pro Glu Glu Glu Val Ser Leu Ser Lys
                485                 490                 495 acg gtg atg aaa ttc tgg gcc aac ttt gct cgc agt ggg aac ccc aat      1536
Thr Val Met Lys Phe Trp Ala Asn Phe Ala Arg Ser Gly Asn Pro Asn
        500                 505                 510 ggg gag ggg ctg ccc cat tgg ccg atg tac gac cag gaa gaa ggg tac      1584
Gly Glu Gly Leu Pro His Trp Pro Met Tyr Asp Gln Glu Glu Gly Tyr
                515                 520                 525 ctt cag atc ggc gtc aac acc cag gca gcc aag agg ctg aaa ggt gaa      1632
Leu Gln Ile Gly Val Asn Thr Gln Ala Ala Lys Arg Leu Lys Gly Glu
    530                 535                 540 gaa gtg gcc ttc tgg aac gat ctc ctg tcc aag gag gca gca aag aag      1680
Glu Val Ala Phe Trp Asn Asp Leu Leu Ser Lys Glu Ala Ala Lys Lys
545                 550                 555                 560 cca ccc aag ata aag tga                                              1698
Pro Pro Lys Ile Lys
                565

<210> SEQ ID NO 4
<211> LENGTH: 565
<212> TYPE: PRT
<213> ORGANISM: Artificial
<220> FEATURE:
<223> OTHER INFORMATION: Synthetic Construct

<400> SEQUENCE: 4

Met Gly Ser Ser His His His His His His Ser Ser Gly Leu Val Pro
1               5                   10                  15

Arg Gly Ser His Met Gly Gln Pro Ala Ser Pro Val Val Asp Thr
            20                  25                  30

Ala Gln Gly Arg Val Leu Gly Lys Tyr Val Ser Leu Glu Gly Leu Ala
        35                  40                  45

Gln Pro Val Ala Val Phe Leu Gly Val Pro Phe Ala Lys Pro Pro Leu
    50                  55                  60

Gly Ser Leu Arg Phe Ala Pro Pro Gln Pro Ala Glu Pro Trp Ser Phe
65                  70                  75                  80

Val Lys Asn Thr Thr Ser Tyr Pro Pro Met Cys Cys Gln Asp Pro Val
```

```
                    85                  90                  95
Val Glu Gln Met Thr Ser Asp Leu Phe Thr Asn Gly Lys Glu Arg Leu
                100                 105                 110

Thr Leu Glu Phe Ser Glu Asp Cys Leu Tyr Leu Asn Ile Tyr Thr Pro
            115                 120                 125

Ala Asp Leu Thr Lys Arg Gly Arg Leu Pro Val Met Val Trp Ile His
        130                 135                 140

Gly Gly Gly Leu Val Leu Gly Gly Ala Pro Met Tyr Asp Gly Val Val
145                 150                 155                 160

Leu Ala Ala His Glu Asn Val Val Val Ala Ile Gln Tyr Arg Leu
                165                 170                 175

Gly Ile Trp Gly Phe Phe Ser Thr Gly Asp Glu His Ser Arg Gly Asn
            180                 185                 190

Trp Gly His Leu Asp Gln Val Ala Ala Leu His Trp Val Gln Glu Asn
        195                 200                 205

Ile Ala Asn Phe Gly Gly Asp Pro Gly Ser Val Thr Ile Phe Gly Glu
        210                 215                 220

Ser Ala Gly Gly Glu Ser Val Ser Val Leu Val Leu Ser Pro Leu Ala
225                 230                 235                 240

Lys Asn Leu Phe His Arg Ala Ile Ser Glu Ser Gly Val Ala Leu Thr
                245                 250                 255

Val Ala Leu Val Arg Lys Asp Met Lys Ala Ala Lys Gln Ile Ala
            260                 265                 270

Val Leu Ala Gly Cys Lys Thr Thr Thr Ser Ala Val Phe Val His Cys
        275                 280                 285

Leu Arg Gln Lys Ser Glu Asp Glu Leu Leu Asp Leu Thr Leu Lys Met
        290                 295                 300

Lys Phe Leu Thr Leu Asp Phe His Gly Asp Gln Arg Glu Ser His Pro
305                 310                 315                 320

Phe Leu Pro Thr Val Val Asp Gly Val Leu Leu Pro Lys Met Pro Glu
                325                 330                 335

Glu Ile Leu Ala Glu Lys Asp Phe Asn Thr Val Pro Tyr Ile Val Gly
            340                 345                 350

Ile Asn Lys Gln Glu Phe Gly Trp Leu Leu Pro Thr Met Met Gly Phe
        355                 360                 365

Pro Leu Ser Glu Gly Lys Leu Asp Gln Lys Thr Ala Thr Ser Leu Leu
        370                 375                 380

Trp Lys Ser Tyr Pro Ile Ala Asn Ile Pro Glu Glu Leu Thr Pro Val
385                 390                 395                 400

Ala Thr Asp Lys Tyr Leu Gly Gly Thr Asp Asp Pro Val Lys Lys Lys
                405                 410                 415

Asp Leu Phe Leu Asp Leu Met Gly Asp Val Val Phe Gly Val Pro Ser
            420                 425                 430

Val Thr Val Ala Arg Gln His Arg Asp Ala Gly Ala Pro Thr Tyr Met
        435                 440                 445

Tyr Glu Phe Gln Tyr Arg Pro Ser Phe Ser Ser Asp Lys Lys Pro Lys
        450                 455                 460

Thr Val Ile Gly Asp His Gly Asp Glu Ile Phe Ser Val Phe Gly Ala
465                 470                 475                 480

Pro Phe Leu Arg Gly Asp Ala Pro Glu Glu Val Ser Leu Ser Lys
                485                 490                 495

Thr Val Met Lys Phe Trp Ala Asn Phe Ala Arg Ser Gly Asn Pro Asn
            500                 505                 510
```

-continued

```
Gly Glu Gly Leu Pro His Trp Pro Met Tyr Asp Gln Glu Glu Gly Tyr
            515                 520                 525

Leu Gln Ile Gly Val Asn Thr Gln Ala Ala Lys Arg Leu Lys Gly Glu
        530                 535                 540

Glu Val Ala Phe Trp Asn Asp Leu Leu Ser Lys Glu Ala Ala Lys Lys
545                 550                 555                 560

Pro Pro Lys Ile Lys
            565

<210> SEQ ID NO 5
<211> LENGTH: 1698
<212> TYPE: DNA
<213> ORGANISM: Artificial
<220> FEATURE:
<223> OTHER INFORMATION: PLE mutant
<220> FEATURE:
<221> NAME/KEY: CDS
<222> LOCATION: (1)..(1698)

<400> SEQUENCE: 5 atg ggc agc agc cat cat cat cat cat cac agc agc ggc ctg gtg ccg      48
Met Gly Ser Ser His His His His His His Ser Ser Gly Leu Val Pro
1               5                   10                  15 cgc ggc agc cat atg ggg cag cca gcc tcg ccg cct gtt gtg gac act      96
Arg Gly Ser His Met Gly Gln Pro Ala Ser Pro Pro Val Val Asp Thr
            20                  25                  30 gcc cag ggc cga gtc ctg ggg aag tac gtc agc tta gaa ggc ctg gca     144
Ala Gln Gly Arg Val Leu Gly Lys Tyr Val Ser Leu Glu Gly Leu Ala
        35                  40                  45 cag ccg gtg gcc gtc ttc ctg gga gtc cct ttt gcc aag ccc cct ctc     192
Gln Pro Val Ala Val Phe Leu Gly Val Pro Phe Ala Lys Pro Pro Leu
    50                  55                  60 gga tcc ttg agg ttt gct ccg ccg cag cct gca gaa cca tgg agc ttc     240
Gly Ser Leu Arg Phe Ala Pro Pro Gln Pro Ala Glu Pro Trp Ser Phe
65                  70                  75                  80 gtg aag aac acc acc tcc tac cct ccc atg tgc tgc cag gac cca gta     288
Val Lys Asn Thr Thr Ser Tyr Pro Pro Met Cys Cys Gln Asp Pro Val
                85                  90                  95 gcg ggg cag atg acc tca gat cta ttt acc aac aga aag gag agg ctc     336
Ala Gly Gln Met Thr Ser Asp Leu Phe Thr Asn Arg Lys Glu Arg Leu
            100                 105                 110 att ccg gag ttt tct gaa gac tgt ctc tac cta aat att tac acc cct     384
Ile Pro Glu Phe Ser Glu Asp Cys Leu Tyr Leu Asn Ile Tyr Thr Pro
        115                 120                 125 gct gac ctg aca aag agg ggc aga ctg ccg gtg atg gtg tgg atc cac     432
Ala Asp Leu Thr Lys Arg Gly Arg Leu Pro Val Met Val Trp Ile His
    130                 135                 140 gga gga ggt ctg gtg gtg ggc ggg gct tcc acc tat gat gga ctg gcc     480
Gly Gly Gly Leu Val Val Gly Gly Ala Ser Thr Tyr Asp Gly Leu Ala
145                 150                 155                 160 ctc gct gcg cat gaa aac gtg gtg gtg gcc atc cag tac cgc ctg         528
Leu Ala Ala His Glu Asn Val Val Val Ala Ile Gln Tyr Arg Leu
                165                 170                 175 ggc atc tgg gga ttc ttc agc aca ggg gac gaa cac agc cgg ggc aac     576
Gly Ile Trp Gly Phe Phe Ser Thr Gly Asp Glu His Ser Arg Gly Asn
            180                 185                 190 tgg ggt cac ttg gac cag gtg gcc gca ctg cac tgg gtc cag gag aac     624
Trp Gly His Leu Asp Gln Val Ala Ala Leu His Trp Val Gln Glu Asn
        195                 200                 205 atc gcc aac ttt gga ggc gac cca ggc tct gtg acc atc ttt gga gag     672
Ile Ala Asn Phe Gly Gly Asp Pro Gly Ser Val Thr Ile Phe Gly Glu
    210                 215                 220
```

```
tca gca gga ggg gaa agt gtc tct gtt ctg gtg ttg tct ccc ttg gcc      720
Ser Ala Gly Gly Glu Ser Val Ser Val Leu Val Leu Ser Pro Leu Ala
225                 230                 235                 240 aag aac ctc ttc cac cgg gcc atc tct gag agt ggc gtg gcc ttc act      768
Lys Asn Leu Phe His Arg Ala Ile Ser Glu Ser Gly Val Ala Phe Thr
                245                 250                 255 gct ggc ctg gtc agg aag gac atg aag gct gca gct aag caa att gct      816
Ala Gly Leu Val Arg Lys Asp Met Lys Ala Ala Ala Lys Gln Ile Ala
        260                 265                 270 gtc ctt gct ggg tgt aaa acc acc acg tcg gct gtc ttt gtt cac tgc      864
Val Leu Ala Gly Cys Lys Thr Thr Thr Ser Ala Val Phe Val His Cys
    275                 280                 285 ctg cgc cag aag tcg gag gac gag ctc ttg gac tta acg ctg aag atg      912
Leu Arg Gln Lys Ser Glu Asp Glu Leu Leu Asp Leu Thr Leu Lys Met
290                 295                 300 aaa cct tta act ctt gat ttg cat gga gac ccc aga gag agc cat ccc      960
Lys Pro Leu Thr Leu Asp Leu His Gly Asp Pro Arg Glu Ser His Pro
305                 310                 315                 320 ttc ctg acc act gtg gtg gat gga gtg ctg ctg ccc aag atg cct gaa     1008
Phe Leu Thr Thr Val Val Asp Gly Val Leu Leu Pro Lys Met Pro Glu
                325                 330                 335 gag att ctg gct gaa aag gat ttc aac act gtc ccc tac atc gtg gga     1056
Glu Ile Leu Ala Glu Lys Asp Phe Asn Thr Val Pro Tyr Ile Val Gly
        340                 345                 350 atc aac aag caa gag ttt ggc tgg ctt ctg cca acg atg atg ggc ttc     1104
Ile Asn Lys Gln Glu Phe Gly Trp Leu Leu Pro Thr Met Met Gly Phe
    355                 360                 365 ccc ctc tct gaa ggc aag ctg gac cag aag acg gcc acg tca ctc ctg     1152
Pro Leu Ser Glu Gly Lys Leu Asp Gln Lys Thr Ala Thr Ser Leu Leu
370                 375                 380 tgg aag tcc tac ccc atc gct aac atc cct gag gaa ctg act cca gtg     1200
Trp Lys Ser Tyr Pro Ile Ala Asn Ile Pro Glu Glu Leu Thr Pro Val
385                 390                 395                 400 gcc act gac aag tat ttg ggg ggg aca gac gac ccc gtc aaa aag aaa     1248
Ala Thr Asp Lys Tyr Leu Gly Gly Thr Asp Asp Pro Val Lys Lys Lys
                405                 410                 415 gac ctg ttc ctg gac ttg atg ggg gat gtg gtg ttt ggt gtc cca tct     1296
Asp Leu Phe Leu Asp Leu Met Gly Asp Val Val Phe Gly Val Pro Ser
        420                 425                 430 gtg acg gtg gcc cgt caa cac aga gat gca gga gcc ccc acc tac atg     1344
Val Thr Val Ala Arg Gln His Arg Asp Ala Gly Ala Pro Thr Tyr Met
    435                 440                 445 tat gag ttt cag tat cgc cca agc ttc tca tcg gac aag aaa ccc aag     1392
Tyr Glu Phe Gln Tyr Arg Pro Ser Phe Ser Ser Asp Lys Lys Pro Lys
450                 455                 460 acg gtg atc ggg gac cac ggg gat gag atc ttc tcc gtc ttt ggg gct     1440
Thr Val Ile Gly Asp His Gly Asp Glu Ile Phe Ser Val Phe Gly Ala
465                 470                 475                 480 cca ttt tta aga ggc gat gcc cca gaa gag gag gtc agt ctc agc aag     1488
Pro Phe Leu Arg Gly Asp Ala Pro Glu Glu Glu Val Ser Leu Ser Lys
                485                 490                 495 acg gtg atg aaa ttc tgg gcc aac ttt gct cgc agt ggg aac ccc aat     1536
Thr Val Met Lys Phe Trp Ala Asn Phe Ala Arg Ser Gly Asn Pro Asn
        500                 505                 510 ggg gag ggg ctg ccc cat tgg ccg atg tac gac cag gaa gaa ggg tac     1584
Gly Glu Gly Leu Pro His Trp Pro Met Tyr Asp Gln Glu Glu Gly Tyr
    515                 520                 525 ctt cag atc ggc gtc aac acc cag gca gcc aag agg ctg aaa ggt gaa     1632
Leu Gln Ile Gly Val Asn Thr Gln Ala Ala Lys Arg Leu Lys Gly Glu
530                 535                 540
```

```
gaa gtg gcc ttc tgg aac gat ctc ctg tcc aag gag gca gca aag aag    1680
Glu Val Ala Phe Trp Asn Asp Leu Leu Ser Lys Glu Ala Ala Lys Lys
545                 550                 555                 560 cca ccc aag ata aag tga                                            1698
Pro Pro Lys Ile Lys
            565
```

<210> SEQ ID NO 6
<211> LENGTH: 565
<212> TYPE: PRT
<213> ORGANISM: Artificial
<220> FEATURE:
<223> OTHER INFORMATION: Synthetic Construct

<400> SEQUENCE: 6

```
Met Gly Ser Ser His His His His His Ser Ser Gly Leu Val Pro
1               5                   10                  15

Arg Gly Ser His Met Gly Gln Pro Ala Ser Pro Val Val Asp Thr
                20                  25                  30

Ala Gln Gly Arg Val Leu Gly Lys Tyr Val Ser Leu Glu Gly Leu Ala
            35                  40                  45

Gln Pro Val Ala Val Phe Leu Gly Val Pro Phe Ala Lys Pro Pro Leu
50                  55                  60

Gly Ser Leu Arg Phe Ala Pro Pro Gln Pro Ala Glu Pro Trp Ser Phe
65                  70                  75                  80

Val Lys Asn Thr Thr Ser Tyr Pro Pro Met Cys Cys Gln Asp Pro Val
                85                  90                  95

Ala Gly Gln Met Thr Ser Asp Leu Phe Thr Asn Arg Lys Glu Arg Leu
            100                 105                 110

Ile Pro Glu Phe Ser Glu Asp Cys Leu Tyr Leu Asn Ile Tyr Thr Pro
        115                 120                 125

Ala Asp Leu Thr Lys Arg Gly Arg Leu Pro Val Met Val Trp Ile His
130                 135                 140

Gly Gly Gly Leu Val Val Gly Gly Ala Ser Thr Tyr Asp Gly Leu Ala
145                 150                 155                 160

Leu Ala Ala His Glu Asn Val Val Val Ala Ile Gln Tyr Arg Leu
                165                 170                 175

Gly Ile Trp Gly Phe Phe Ser Thr Gly Asp Glu His Ser Arg Gly Asn
            180                 185                 190

Trp Gly His Leu Asp Gln Val Ala Ala Leu His Trp Val Gln Glu Asn
        195                 200                 205

Ile Ala Asn Phe Gly Gly Asp Pro Gly Ser Val Thr Ile Phe Gly Glu
    210                 215                 220

Ser Ala Gly Gly Glu Ser Val Ser Val Leu Val Leu Ser Pro Leu Ala
225                 230                 235                 240

Lys Asn Leu Phe His Arg Ala Ile Ser Glu Ser Gly Val Ala Phe Thr
                245                 250                 255

Ala Gly Leu Val Arg Lys Asp Met Lys Ala Ala Lys Gln Ile Ala
            260                 265                 270

Val Leu Ala Gly Cys Lys Thr Thr Thr Ser Ala Val Phe Val His Cys
275                 280                 285

Leu Arg Gln Lys Ser Glu Asp Glu Leu Leu Asp Leu Thr Leu Lys Met
    290                 295                 300

Lys Pro Leu Thr Leu Asp Leu His Gly Asp Pro Arg Glu Ser His Pro
305                 310                 315                 320

Phe Leu Thr Thr Val Val Asp Gly Val Leu Leu Pro Lys Met Pro Glu
```

```
                     325                 330                 335
Glu Ile Leu Ala Glu Lys Asp Phe Asn Thr Val Pro Tyr Ile Val Gly
            340                 345                 350

Ile Asn Lys Gln Glu Phe Gly Trp Leu Leu Pro Thr Met Met Gly Phe
            355                 360                 365

Pro Leu Ser Glu Gly Lys Leu Asp Gln Lys Thr Ala Thr Ser Leu Leu
            370                 375                 380

Trp Lys Ser Tyr Pro Ile Ala Asn Ile Pro Glu Glu Leu Thr Pro Val
385                 390                 395                 400

Ala Thr Asp Lys Tyr Leu Gly Gly Thr Asp Pro Val Lys Lys
                405                 410                 415

Asp Leu Phe Leu Asp Leu Met Gly Asp Val Val Phe Gly Val Pro Ser
                420                 425                 430

Val Thr Val Ala Arg Gln His Arg Asp Ala Gly Ala Pro Thr Tyr Met
            435                 440                 445

Tyr Glu Phe Gln Tyr Arg Pro Ser Phe Ser Ser Asp Lys Lys Pro Lys
            450                 455                 460

Thr Val Ile Gly Asp His Gly Asp Glu Ile Phe Ser Val Phe Gly Ala
465                 470                 475                 480

Pro Phe Leu Arg Gly Asp Ala Pro Glu Glu Val Ser Leu Ser Lys
                485                 490                 495

Thr Val Met Lys Phe Trp Ala Asn Phe Ala Arg Ser Gly Asn Pro Asn
            500                 505                 510

Gly Glu Gly Leu Pro His Trp Pro Met Tyr Asp Gln Glu Gly Tyr
            515                 520                 525

Leu Gln Ile Gly Val Asn Thr Gln Ala Ala Lys Arg Leu Lys Gly Glu
            530                 535                 540

Glu Val Ala Phe Trp Asn Asp Leu Leu Ser Lys Glu Ala Ala Lys Lys
545                 550                 555                 560

Pro Pro Lys Ile Lys
                565

<210> SEQ ID NO 7
<211> LENGTH: 1698
<212> TYPE: DNA
<213> ORGANISM: Artificial
<220> FEATURE:
<223> OTHER INFORMATION: PLE mutant
<220> FEATURE:
<221> NAME/KEY: CDS
<222> LOCATION: (1)..(1698)

<400> SEQUENCE: 7 atg ggc agc agc cat cat cat cat cat cac agc agc ggc ctg gtg ccg    48
Met Gly Ser Ser His His His His His His Ser Ser Gly Leu Val Pro
1               5                   10                  15 cgc ggc agc cat atg ggg cag cca gcc tcg ccg cct gtt gtg gac act    96
Arg Gly Ser His Met Gly Gln Pro Ala Ser Pro Pro Val Val Asp Thr
            20                  25                  30 gcc cag ggc cga gtc ctg ggg aag tac gtc agc tta gaa ggc ctg gca   144
Ala Gln Gly Arg Val Leu Gly Lys Tyr Val Ser Leu Glu Gly Leu Ala
        35                  40                  45 cag ccg gtg gcc gtc ttc ctg gga gtc cct ttt gcc aag ccc cct ctc   192
Gln Pro Val Ala Val Phe Leu Gly Val Pro Phe Ala Lys Pro Pro Leu
    50                  55                  60 gga tcc ttg agg ttt gct ccg ccg cag cct gca gaa cca tgg agc ttc   240
Gly Ser Leu Arg Phe Ala Pro Pro Gln Pro Ala Glu Pro Trp Ser Phe
65                  70                  75                  80
```

```
gtg aag aac acc acc tcc tac cct ccc atg tgc tgc cag gac cca gta      288
Val Lys Asn Thr Thr Ser Tyr Pro Pro Met Cys Cys Gln Asp Pro Val
                85              90              95 gcg ggg cag atg acc tca gat cta ttt acc aac aga aag gag agg ctc      336
Ala Gly Gln Met Thr Ser Asp Leu Phe Thr Asn Arg Lys Glu Arg Leu
            100             105             110 att ccg gag ttt tct gaa gac tgt ctc tac cta aat att tac acc cct      384
Ile Pro Glu Phe Ser Glu Asp Cys Leu Tyr Leu Asn Ile Tyr Thr Pro
        115             120             125 gct gac ctg aca aag agg ggc aga ctg ccg gtg atg gtg tgg atc cac      432
Ala Asp Leu Thr Lys Arg Gly Arg Leu Pro Val Met Val Trp Ile His
    130             135             140 gga gga ggt ctg gtg gtg ggc ggg gct tcc acc tat gat gga ctg gcc      480
Gly Gly Gly Leu Val Val Gly Gly Ala Ser Thr Tyr Asp Gly Leu Ala
145             150             155             160 ctc gct gcg cat gaa aac gtg gtg gtg gtg gcc atc cag tac cgc ctg      528
Leu Ala Ala His Glu Asn Val Val Val Val Ala Ile Gln Tyr Arg Leu
                165             170             175 ggc atc tgg gga ttc ttc agc aca ggg gac gaa cac agc cgg ggc aac      576
Gly Ile Trp Gly Phe Phe Ser Thr Gly Asp Glu His Ser Arg Gly Asn
            180             185             190 tgg ggt cac ttg gac cag gtg gcc gca ctg cac tgg gtc cag gag aac      624
Trp Gly His Leu Asp Gln Val Ala Ala Leu His Trp Val Gln Glu Asn
        195             200             205 atc gcc aac ttt gga ggc gac cca ggc tct gtg acc atc ttt gga gag      672
Ile Ala Asn Phe Gly Gly Asp Pro Gly Ser Val Thr Ile Phe Gly Glu
    210             215             220 tca gca gga ggg gaa agt gtc tct gtt ctg gtg ttg tct ccc ttg gcc      720
Ser Ala Gly Gly Glu Ser Val Ser Val Leu Val Leu Ser Pro Leu Ala
225             230             235             240 aag aac ctc ttc cac cgg gcc atc tct gag agt ggc gtg gcc ttc act      768
Lys Asn Leu Phe His Arg Ala Ile Ser Glu Ser Gly Val Ala Phe Thr
                245             250             255 gct ggc ctg gtc agg aag gac atg aag gct gca gct aag caa att gct      816
Ala Gly Leu Val Arg Lys Asp Met Lys Ala Ala Ala Lys Gln Ile Ala
            260             265             270 gtc ctt gct ggg tgt aaa acc acc acc tcg gct gtc ttt gtt cac tgc      864
Val Leu Ala Gly Cys Lys Thr Thr Thr Ser Ala Val Phe Val His Cys
        275             280             285 ctg cgc cag aag tcg gag gac gag ctc ttg gac tta acg ctg aag atg      912
Leu Arg Gln Lys Ser Glu Asp Glu Leu Leu Asp Leu Thr Leu Lys Met
    290             295             300 aaa ttt ttc gct ctt gat ttg cat gga gac ccc aga gag agc cat ccc      960
Lys Phe Phe Ala Leu Asp Leu His Gly Asp Pro Arg Glu Ser His Pro
305             310             315             320 ttc ctg acc act gtg gtg gat gga gtg ctg ctc ccc aag atg cct gaa     1008
Phe Leu Thr Thr Val Val Asp Gly Val Leu Leu Pro Lys Met Pro Glu
                325             330             335 gag att ctg gct gaa aag gat ttc aac act gtc ccc tac atc gtg gga     1056
Glu Ile Leu Ala Glu Lys Asp Phe Asn Thr Val Pro Tyr Ile Val Gly
            340             345             350 atc aac aag caa gag ttt ggc tgg ctt ctg cca acg atg atg ggc ttc     1104
Ile Asn Lys Gln Glu Phe Gly Trp Leu Leu Pro Thr Met Met Gly Phe
        355             360             365 ccc ctc tct gaa ggc aag ctg gac cag aag acg gcc acg tca ctc ctg     1152
Pro Leu Ser Glu Gly Lys Leu Asp Gln Lys Thr Ala Thr Ser Leu Leu
    370             375             380 tgg aag tcc tac ccc atc gct aac atc cct gag gaa ctg act cca gtg     1200
Trp Lys Ser Tyr Pro Ile Ala Asn Ile Pro Glu Glu Leu Thr Pro Val
385             390             395             400
```

```
gcc act gac aag tat ttg ggg ggg aca gac gac ccc gtc aaa aag aaa       1248
Ala Thr Asp Lys Tyr Leu Gly Gly Thr Asp Asp Pro Val Lys Lys Lys
            405                 410                 415 gac ctg ttc ctg gac ttg atg ggg gat gtg gtg ttt ggt gtc cca tct       1296
Asp Leu Phe Leu Asp Leu Met Gly Asp Val Val Phe Gly Val Pro Ser
        420                 425                 430 gtg acg gtg gcc cgt caa cac aga gat gca gga gcc ccc acc tac atg       1344
Val Thr Val Ala Arg Gln His Arg Asp Ala Gly Ala Pro Thr Tyr Met
    435                 440                 445 tat gag ttt cag tat cgc cca agc ttc tca tcg gac aag aaa ccc aag       1392
Tyr Glu Phe Gln Tyr Arg Pro Ser Phe Ser Ser Asp Lys Lys Pro Lys
450                 455                 460 acg gtg atc ggg gac cac ggg gat gag atc ttc tcc gtc ttt ggg gct       1440
Thr Val Ile Gly Asp His Gly Asp Glu Ile Phe Ser Val Phe Gly Ala
465                 470                 475                 480 cca ttt tta aga ggc gat gcc cca gaa gag gag gtc agt ctc agc aag       1488
Pro Phe Leu Arg Gly Asp Ala Pro Glu Glu Glu Val Ser Leu Ser Lys
                485                 490                 495 acg gtg atg aaa ttc tgg gcc aac ttt gct cgc agt ggg aac ccc aat       1536
Thr Val Met Lys Phe Trp Ala Asn Phe Ala Arg Ser Gly Asn Pro Asn
            500                 505                 510 ggg gag ggg ctg ccc cat tgg ccg atg tac gac cag gaa gaa ggg tac       1584
Gly Glu Gly Leu Pro His Trp Pro Met Tyr Asp Gln Glu Glu Gly Tyr
        515                 520                 525 ctt cag atc ggc gtc aac acc cag gca gcc aag agg ctg aaa ggt gaa       1632
Leu Gln Ile Gly Val Asn Thr Gln Ala Ala Lys Arg Leu Lys Gly Glu
    530                 535                 540 gaa gtg gcc ttc tgg aac gat ctc ctg tcc aag gag gca gca aag aag       1680
Glu Val Ala Phe Trp Asn Asp Leu Leu Ser Lys Glu Ala Ala Lys Lys
545                 550                 555                 560 cca ccc aag ata aag tga                                               1698
Pro Pro Lys Ile Lys
                565

<210> SEQ ID NO 8
<211> LENGTH: 565
<212> TYPE: PRT
<213> ORGANISM: Artificial
<220> FEATURE:
<223> OTHER INFORMATION: Synthetic Construct

<400> SEQUENCE: 8

Met Gly Ser Ser His His His His His His Ser Ser Gly Leu Val Pro
1               5                   10                  15

Arg Gly Ser His Met Gly Gln Pro Ala Ser Pro Val Val Asp Thr
            20                  25                  30

Ala Gln Gly Arg Val Leu Gly Lys Tyr Val Ser Leu Glu Gly Leu Ala
        35                  40                  45

Gln Pro Val Ala Val Phe Leu Gly Val Pro Phe Ala Lys Pro Pro Leu
    50                  55                  60

Gly Ser Leu Arg Phe Ala Pro Pro Gln Pro Ala Glu Pro Trp Ser Phe
65                  70                  75                  80

Val Lys Asn Thr Thr Ser Tyr Pro Pro Met Cys Cys Gln Asp Pro Val
                85                  90                  95

Ala Gly Gln Met Thr Ser Asp Leu Phe Thr Asn Arg Lys Glu Arg Leu
            100                 105                 110

Ile Pro Glu Phe Ser Glu Asp Cys Leu Tyr Leu Asn Ile Tyr Thr Pro
        115                 120                 125

Ala Asp Leu Thr Lys Arg Gly Arg Leu Pro Val Met Val Trp Ile His
    130                 135                 140
```

-continued

```
Gly Gly Gly Leu Val Val Gly Ala Ser Thr Tyr Asp Gly Leu Ala
145                 150                 155                 160

Leu Ala Ala His Glu Asn Val Val Val Ala Ile Gln Tyr Arg Leu
                165                 170                 175

Gly Ile Trp Gly Phe Phe Ser Thr Gly Asp Glu His Ser Arg Gly Asn
            180                 185                 190

Trp Gly His Leu Asp Gln Val Ala Ala Leu His Trp Val Gln Glu Asn
        195                 200                 205

Ile Ala Asn Phe Gly Gly Asp Pro Gly Ser Val Thr Ile Phe Gly Glu
    210                 215                 220

Ser Ala Gly Gly Glu Ser Val Ser Val Leu Val Leu Ser Pro Leu Ala
225                 230                 235                 240

Lys Asn Leu Phe His Arg Ala Ile Ser Glu Ser Gly Val Ala Phe Thr
                245                 250                 255

Ala Gly Leu Val Arg Lys Asp Met Lys Ala Ala Lys Gln Ile Ala
            260                 265                 270

Val Leu Ala Gly Cys Lys Thr Thr Thr Ser Ala Val Phe Val His Cys
        275                 280                 285

Leu Arg Gln Lys Ser Glu Asp Glu Leu Leu Asp Leu Thr Leu Lys Met
    290                 295                 300

Lys Phe Phe Ala Leu Asp Leu His Gly Asp Pro Arg Glu Ser His Pro
305                 310                 315                 320

Phe Leu Thr Thr Val Asp Gly Val Leu Leu Pro Lys Met Pro Glu
                325                 330                 335

Glu Ile Leu Ala Glu Lys Asp Phe Asn Thr Val Pro Tyr Ile Val Gly
            340                 345                 350

Ile Asn Lys Gln Glu Phe Gly Trp Leu Leu Pro Thr Met Met Gly Phe
        355                 360                 365

Pro Leu Ser Glu Gly Lys Leu Asp Gln Lys Thr Ala Thr Ser Leu Leu
    370                 375                 380

Trp Lys Ser Tyr Pro Ile Ala Asn Ile Pro Glu Glu Leu Thr Pro Val
385                 390                 395                 400

Ala Thr Asp Lys Tyr Leu Gly Gly Thr Asp Asp Pro Val Lys Lys Lys
                405                 410                 415

Asp Leu Phe Leu Asp Leu Met Gly Asp Val Val Phe Gly Val Pro Ser
            420                 425                 430

Val Thr Val Ala Arg Gln His Arg Asp Ala Gly Ala Pro Thr Tyr Met
        435                 440                 445

Tyr Glu Phe Gln Tyr Arg Pro Ser Phe Ser Ser Asp Lys Lys Pro Lys
    450                 455                 460

Thr Val Ile Gly Asp His Gly Asp Glu Ile Phe Ser Val Phe Gly Ala
465                 470                 475                 480

Pro Phe Leu Arg Gly Asp Ala Pro Glu Glu Glu Val Ser Leu Ser Lys
                485                 490                 495

Thr Val Met Lys Phe Trp Ala Asn Phe Ala Arg Ser Gly Asn Pro Asn
            500                 505                 510

Gly Glu Gly Leu Pro His Trp Pro Met Tyr Asp Gln Glu Glu Gly Tyr
        515                 520                 525

Leu Gln Ile Gly Val Asn Thr Gln Ala Ala Lys Arg Leu Lys Gly Glu
    530                 535                 540

Glu Val Ala Phe Trp Asn Asp Leu Leu Ser Lys Glu Ala Ala Lys Lys
545                 550                 555                 560

Pro Pro Lys Ile Lys
```

<210> SEQ ID NO 9
<211> LENGTH: 1698
<212> TYPE: DNA
<213> ORGANISM: Artificial
<220> FEATURE:
<223> OTHER INFORMATION: PLE mutant
<220> FEATURE:
<221> NAME/KEY: CDS
<222> LOCATION: (1)..(1698)

<400> SEQUENCE: 9

```
atg ggc agc agc cat cat cat cat cat cac agc agc ggc ctg gtg ccg        48
Met Gly Ser Ser His His His His His His Ser Ser Gly Leu Val Pro
1               5                   10                  15 cgc ggc agc cat atg ggg cag cca gcc tcg ccg cct gtt gtg gac act        96
Arg Gly Ser His Met Gly Gln Pro Ala Ser Pro Pro Val Val Asp Thr
            20                  25                  30 gcc cag ggc cga gtc ctg ggg aag tac gtc agc tta gaa ggc ctg gca       144
Ala Gln Gly Arg Val Leu Gly Lys Tyr Val Ser Leu Glu Gly Leu Ala
        35                  40                  45 cag ccg gtg gcc gtc ttc ctg gga gtc cct ttt gcc aag ccc cct ctc       192
Gln Pro Val Ala Val Phe Leu Gly Val Pro Phe Ala Lys Pro Pro Leu
    50                  55                  60 gga tcc ttg agg ttt gct ccg ccg cag cct gca gaa cca tgg agc ttc       240
Gly Ser Leu Arg Phe Ala Pro Pro Gln Pro Ala Glu Pro Trp Ser Phe
65                  70                  75                  80 gtg aag aac acc acc tcc tac cct ccc atg tgc tgc caa gag cca att       288
Val Lys Asn Thr Thr Ser Tyr Pro Pro Met Cys Cys Gln Glu Pro Ile
                85                  90                  95 ggg gga cag atg ctc tca gat cta ttt acc aac aga aag gag agg ctc       336
Gly Gly Gln Met Leu Ser Asp Leu Phe Thr Asn Arg Lys Glu Arg Leu
            100                 105                 110 att ccg gag ttt tct gaa gac tgt ctc tac cta aat att tac acc cct       384
Ile Pro Glu Phe Ser Glu Asp Cys Leu Tyr Leu Asn Ile Tyr Thr Pro
        115                 120                 125 gct gac ctg aca aag agg ggc aga ctg ccg gtg atg gtg tgg atc cac       432
Ala Asp Leu Thr Lys Arg Gly Arg Leu Pro Val Met Val Trp Ile His
    130                 135                 140 gga gga ggt ctg gtg gtg ggc ggg gct tcc acc tat gat gga ctg gcc       480
Gly Gly Gly Leu Val Val Gly Gly Ala Ser Thr Tyr Asp Gly Leu Ala
145                 150                 155                 160 ctc gct gcg cat gaa aac gtg gtg gtg gcc atc cag tac cgc ctg            528
Leu Ala Ala His Glu Asn Val Val Val Val Ala Ile Gln Tyr Arg Leu
                165                 170                 175 ggc atc tgg gga ttc ttc agc aca ggg gac gaa cac agc cgg ggc aac       576
Gly Ile Trp Gly Phe Phe Ser Thr Gly Asp Glu His Ser Arg Gly Asn
            180                 185                 190 tgg ggt cac ttg gac cag gtg gcc gca ctg cac tgg gtc cag gag aac       624
Trp Gly His Leu Asp Gln Val Ala Ala Leu His Trp Val Gln Glu Asn
        195                 200                 205 atc gcc aac ttt gga ggc gac cca ggc tct gtg acc atc ttt gga gag       672
Ile Ala Asn Phe Gly Gly Asp Pro Gly Ser Val Thr Ile Phe Gly Glu
    210                 215                 220 tca gca gga ggg gaa agt gtc tct gtt ctg gtg ttg tct ccc ttg gcc       720
Ser Ala Gly Gly Glu Ser Val Ser Val Leu Val Leu Ser Pro Leu Ala
225                 230                 235                 240 aag aac ctc ttc cac cgg gcc atc tct gag agt ggc gtg gcc ttc act       768
Lys Asn Leu Phe His Arg Ala Ile Ser Glu Ser Gly Val Ala Phe Thr
                245                 250                 255 gct ggc ctg gtc agg aag gac atg aag gct gca gct aag caa att gct       816
```

```
Ala Gly Leu Val Arg Lys Asp Met Lys Ala Ala Lys Gln Ile Ala
            260                 265                 270 gtc ctt gct ggg tgt aaa acc acc acc tcg gct gtc ttt gtt cac tgc    864
Val Leu Ala Gly Cys Lys Thr Thr Thr Ser Ala Val Phe Val His Cys
        275                 280                 285 ctg cgc cag aag tcg gag gac gag ctc ttg gac tta acg ctg aag atg    912
Leu Arg Gln Lys Ser Glu Asp Glu Leu Leu Asp Leu Thr Leu Lys Met
    290                 295                 300 aaa cct tta act ctt gat ttg cat gga gac ccc aga gag agc cat ccc    960
Lys Pro Leu Thr Leu Asp Leu His Gly Asp Pro Arg Glu Ser His Pro
305                 310                 315                 320 ttc ctg acc act gtg gtg gat gga gtg ctg ctg ccc aag atg cct gaa    1008
Phe Leu Thr Thr Val Val Asp Gly Val Leu Leu Pro Lys Met Pro Glu
                325                 330                 335 gag att ctg gct gaa aag gat ttc aac act gtc ccc tac atc gtg gga    1056
Glu Ile Leu Ala Glu Lys Asp Phe Asn Thr Val Pro Tyr Ile Val Gly
            340                 345                 350 atc aac aag caa gag ttt ggc tgg ctt ctg cca acg atg atg ggc ttc    1104
Ile Asn Lys Gln Glu Phe Gly Trp Leu Leu Pro Thr Met Met Gly Phe
        355                 360                 365 ccc ctc tct gaa ggc aag ctg gac cag aag acg gcc acg tca ctc ctg    1152
Pro Leu Ser Glu Gly Lys Leu Asp Gln Lys Thr Ala Thr Ser Leu Leu
    370                 375                 380 tgg aag tcc tac ccc atc gct aac atc cct gag gaa ctg act cca gtg    1200
Trp Lys Ser Tyr Pro Ile Ala Asn Ile Pro Glu Glu Leu Thr Pro Val
385                 390                 395                 400 gcc act gac aag tat ttg ggg ggg aca gac gac ccc gtc aaa aag aaa    1248
Ala Thr Asp Lys Tyr Leu Gly Gly Thr Asp Asp Pro Val Lys Lys Lys
                405                 410                 415 gac ctg ttc ctg gac ttg atg ggg gat gtg gtg ttt ggt gtc cca tct    1296
Asp Leu Phe Leu Asp Leu Met Gly Asp Val Val Phe Gly Val Pro Ser
            420                 425                 430 gtg acg gtg gcc cgt caa cac aga gat gca gga gcc ccc acc tac atg    1344
Val Thr Val Ala Arg Gln His Arg Asp Ala Gly Ala Pro Thr Tyr Met
        435                 440                 445 tat gag ttt cag tat cgc cca agc ttc tca tcg gac aag aaa ccc aag    1392
Tyr Glu Phe Gln Tyr Arg Pro Ser Phe Ser Ser Asp Lys Lys Pro Lys
    450                 455                 460 acg gtg atc ggg gac cac ggg gat gag atc ttc tcc gtc ttt ggt ttt    1440
Thr Val Ile Gly Asp His Gly Asp Glu Ile Phe Ser Val Phe Gly Phe
465                 470                 475                 480 cca ctg tta aaa ggc gat gcc cca gaa gag gag gtc agt ctc agc aag    1488
Pro Leu Leu Lys Gly Asp Ala Pro Glu Glu Glu Val Ser Leu Ser Lys
                485                 490                 495 acg gtg atg aaa ttc tgg gcc aac ttt gct cgc agt ggg aac ccc aat    1536
Thr Val Met Lys Phe Trp Ala Asn Phe Ala Arg Ser Gly Asn Pro Asn
            500                 505                 510 ggg gag ggg ctg ccc cat tgg ccg atg tac gac cag gaa gaa ggg tac    1584
Gly Glu Gly Leu Pro His Trp Pro Met Tyr Asp Gln Glu Glu Gly Tyr
        515                 520                 525 ctt cag atc ggc gtc aac acc cag gca gcc aag agg ctg aaa ggt gaa    1632
Leu Gln Ile Gly Val Asn Thr Gln Ala Ala Lys Arg Leu Lys Gly Glu
    530                 535                 540 gaa gtg gcc ttc tgg aac gat ctc ctg tcc aag gag gca gca aag aag    1680
Glu Val Ala Phe Trp Asn Asp Leu Leu Ser Lys Glu Ala Ala Lys Lys
545                 550                 555                 560 cca ccc aag ata aag tga                                             1698
Pro Pro Lys Ile Lys
                565
```

```
<210> SEQ ID NO 10
<211> LENGTH: 565
<212> TYPE: PRT
<213> ORGANISM: Artificial
<220> FEATURE:
<223> OTHER INFORMATION: Synthetic Construct

<400> SEQUENCE: 10
```

| Met | Gly | Ser | Ser | His | His | His | His | His | His | Ser | Ser | Gly | Leu | Val | Pro |
|---|---|---|---|---|---|---|---|---|---|---|---|---|---|---|---|
| 1 | | | | 5 | | | | | 10 | | | | | 15 | |

| Arg | Gly | Ser | His | Met | Gly | Gln | Pro | Ala | Ser | Pro | Val | Val | Asp | Thr |
|---|---|---|---|---|---|---|---|---|---|---|---|---|---|---|
| | | | 20 | | | | 25 | | | | 30 | | | |

| Ala | Gln | Gly | Arg | Val | Leu | Gly | Lys | Tyr | Val | Ser | Leu | Glu | Gly | Leu | Ala |
|---|---|---|---|---|---|---|---|---|---|---|---|---|---|---|---|
| | | 35 | | | | | 40 | | | | | 45 | | | |

| Gln | Pro | Val | Ala | Val | Phe | Leu | Gly | Val | Pro | Phe | Ala | Lys | Pro | Pro | Leu |
|---|---|---|---|---|---|---|---|---|---|---|---|---|---|---|---|
| | 50 | | | | | 55 | | | | | 60 | | | | |

| Gly | Ser | Leu | Arg | Phe | Ala | Pro | Pro | Gln | Pro | Ala | Glu | Pro | Trp | Ser | Phe |
|---|---|---|---|---|---|---|---|---|---|---|---|---|---|---|---|
| 65 | | | | | 70 | | | | | 75 | | | | | 80 |

| Val | Lys | Asn | Thr | Thr | Ser | Tyr | Pro | Pro | Met | Cys | Cys | Gln | Glu | Pro | Ile |
|---|---|---|---|---|---|---|---|---|---|---|---|---|---|---|---|
| | | | | 85 | | | | | 90 | | | | | 95 | |

| Gly | Gly | Gln | Met | Leu | Ser | Asp | Leu | Phe | Thr | Asn | Arg | Lys | Glu | Arg | Leu |
|---|---|---|---|---|---|---|---|---|---|---|---|---|---|---|---|
| | | | 100 | | | | | 105 | | | | | 110 | | |

| Ile | Pro | Glu | Phe | Ser | Glu | Asp | Cys | Leu | Tyr | Leu | Asn | Ile | Tyr | Thr | Pro |
|---|---|---|---|---|---|---|---|---|---|---|---|---|---|---|---|
| | | | 115 | | | | | 120 | | | | | 125 | | |

| Ala | Asp | Leu | Thr | Lys | Arg | Gly | Arg | Leu | Pro | Val | Met | Val | Trp | Ile | His |
|---|---|---|---|---|---|---|---|---|---|---|---|---|---|---|---|
| | 130 | | | | | 135 | | | | | 140 | | | | |

| Gly | Gly | Gly | Leu | Val | Val | Gly | Gly | Ala | Ser | Thr | Tyr | Asp | Gly | Leu | Ala |
|---|---|---|---|---|---|---|---|---|---|---|---|---|---|---|---|
| 145 | | | | | 150 | | | | | 155 | | | | | 160 |

| Leu | Ala | Ala | His | Glu | Asn | Val | Val | Val | Ala | Ile | Gln | Tyr | Arg | Leu |
|---|---|---|---|---|---|---|---|---|---|---|---|---|---|---|
| | | | | 165 | | | | | 170 | | | | | 175 |

| Gly | Ile | Trp | Gly | Phe | Phe | Ser | Thr | Gly | Asp | Glu | His | Ser | Arg | Gly | Asn |
|---|---|---|---|---|---|---|---|---|---|---|---|---|---|---|---|
| | | | 180 | | | | | 185 | | | | | 190 | | |

| Trp | Gly | His | Leu | Asp | Gln | Val | Ala | Ala | Leu | His | Trp | Val | Gln | Glu | Asn |
|---|---|---|---|---|---|---|---|---|---|---|---|---|---|---|---|
| | | 195 | | | | | 200 | | | | | 205 | | | |

| Ile | Ala | Asn | Phe | Gly | Gly | Asp | Pro | Gly | Ser | Val | Thr | Ile | Phe | Gly | Glu |
|---|---|---|---|---|---|---|---|---|---|---|---|---|---|---|---|
| | 210 | | | | | 215 | | | | | 220 | | | | |

| Ser | Ala | Gly | Gly | Glu | Ser | Val | Ser | Val | Leu | Val | Leu | Ser | Pro | Leu | Ala |
|---|---|---|---|---|---|---|---|---|---|---|---|---|---|---|---|
| 225 | | | | | 230 | | | | | 235 | | | | | 240 |

| Lys | Asn | Leu | Phe | His | Arg | Ala | Ile | Ser | Glu | Ser | Gly | Val | Ala | Phe | Thr |
|---|---|---|---|---|---|---|---|---|---|---|---|---|---|---|---|
| | | | | 245 | | | | | 250 | | | | | 255 | |

| Ala | Gly | Leu | Val | Arg | Lys | Asp | Met | Lys | Ala | Ala | Lys | Gln | Ile | Ala |
|---|---|---|---|---|---|---|---|---|---|---|---|---|---|---|
| | | | 260 | | | | | 265 | | | | | 270 | |

| Val | Leu | Ala | Gly | Cys | Lys | Thr | Thr | Thr | Ser | Ala | Val | Phe | Val | His | Cys |
|---|---|---|---|---|---|---|---|---|---|---|---|---|---|---|---|
| | | 275 | | | | | 280 | | | | | 285 | | | |

| Leu | Arg | Gln | Lys | Ser | Glu | Asp | Glu | Leu | Leu | Asp | Leu | Thr | Leu | Lys | Met |
|---|---|---|---|---|---|---|---|---|---|---|---|---|---|---|---|
| | 290 | | | | | 295 | | | | | 300 | | | | |

| Lys | Pro | Leu | Thr | Leu | Asp | Leu | His | Gly | Asp | Pro | Arg | Glu | Ser | His | Pro |
|---|---|---|---|---|---|---|---|---|---|---|---|---|---|---|---|
| 305 | | | | | 310 | | | | | 315 | | | | | 320 |

| Phe | Leu | Thr | Thr | Val | Val | Asp | Gly | Val | Leu | Leu | Pro | Lys | Met | Pro | Glu |
|---|---|---|---|---|---|---|---|---|---|---|---|---|---|---|---|
| | | | | 325 | | | | | 330 | | | | | 335 | |

| Glu | Ile | Leu | Ala | Glu | Lys | Asp | Phe | Asn | Thr | Val | Pro | Tyr | Ile | Val | Gly |
|---|---|---|---|---|---|---|---|---|---|---|---|---|---|---|---|
| | | | 340 | | | | | 345 | | | | | 350 | | |

| Ile | Asn | Lys | Gln | Glu | Phe | Gly | Trp | Leu | Leu | Pro | Thr | Met | Met | Gly | Phe |
|---|---|---|---|---|---|---|---|---|---|---|---|---|---|---|---|
| | | 355 | | | | | 360 | | | | | 365 | | | |

| Pro | Leu | Ser | Glu | Gly | Lys | Leu | Asp | Gln | Lys | Thr | Ala | Thr | Ser | Leu | Leu |
|---|---|---|---|---|---|---|---|---|---|---|---|---|---|---|---|
| | 370 | | | | | 375 | | | | | 380 | | | | |

```
Trp Lys Ser Tyr Pro Ile Ala Asn Ile Pro Glu Glu Leu Thr Pro Val
385                 390                 395                 400

Ala Thr Asp Lys Tyr Leu Gly Gly Thr Asp Asp Pro Val Lys Lys Lys
                405                 410                 415

Asp Leu Phe Leu Asp Leu Met Gly Asp Val Val Phe Gly Val Pro Ser
            420                 425                 430

Val Thr Val Ala Arg Gln His Arg Asp Ala Gly Ala Pro Thr Tyr Met
        435                 440                 445

Tyr Glu Phe Gln Tyr Arg Pro Ser Phe Ser Ser Asp Lys Lys Pro Lys
    450                 455                 460

Thr Val Ile Gly Asp His Gly Asp Glu Ile Phe Ser Val Phe Gly Phe
465                 470                 475                 480

Pro Leu Leu Lys Gly Asp Ala Pro Glu Glu Glu Val Ser Leu Ser Lys
                485                 490                 495

Thr Val Met Lys Phe Trp Ala Asn Phe Ala Arg Ser Gly Asn Pro Asn
                500                 505                 510

Gly Glu Gly Leu Pro His Trp Pro Met Tyr Asp Gln Glu Glu Gly Tyr
            515                 520                 525

Leu Gln Ile Gly Val Asn Thr Gln Ala Ala Lys Arg Leu Lys Gly Glu
        530                 535                 540

Glu Val Ala Phe Trp Asn Asp Leu Leu Ser Lys Glu Ala Ala Lys Lys
545                 550                 555                 560

Pro Pro Lys Ile Lys
                565

<210> SEQ ID NO 11
<211> LENGTH: 26
<212> TYPE: DNA
<213> ORGANISM: Artificial
<220> FEATURE:
<223> OTHER INFORMATION: Primer

<400> SEQUENCE: 11
cacccatatg gggcagccag cctcgc                                          26

<210> SEQ ID NO 12
<211> LENGTH: 36
<212> TYPE: DNA
<213> ORGANISM: Artificial
<220> FEATURE:
<223> OTHER INFORMATION: Primer

<400> SEQUENCE: 12
ccgctcgagt cactttatct tgggtggctt ctttgc                               36
```